United States Patent
Beight et al.

(10) Patent No.: US 6,992,100 B2
(45) Date of Patent: *Jan. 31, 2006

(54) SPLA$_2$ INHIBITORS

(75) Inventors: Douglas Wade Beight, Frankfort, IN (US); Michael Dean Kinnick, Indianapolis, IN (US); Ho-Shen Lin, Indianapolis, IN (US); John Michael Morin, Jr., Brownsburg, IN (US); Michael Enrico Richett, Indianapolis, IN (US); Daniel Jon Sall, Greenwood, IN (US); Jason Scott Sawyer, Indianapolis, IN (US); John David Jandzinski, Hopewell Junction, NY (US)

(73) Assignee: Eli Lilly and Company, Indianapolis, IN (US)

( * ) Notice: Subject to any disclaimer, the term of this patent is extended or adjusted under 35 U.S.C. 154(b) by 365 days.

This patent is subject to a terminal disclaimer.

(21) Appl. No.: 10/450,745

(22) PCT Filed: Dec. 6, 2001

(86) PCT No.: PCT/US01/43186

§ 371 (c)(1),
(2), (4) Date: Jun. 16, 2003

(87) PCT Pub. No.: WO02/50029

PCT Pub. Date: Jun. 27, 2002

(65) Prior Publication Data

US 2004/0092543 A1 May 13, 2004

(51) Int. Cl.
*A61K 31/403* (2006.01)
*C07D 209/56* (2006.01)
(52) U.S. Cl. .................. 514/410; 548/420
(58) Field of Classification Search ........... 548/420; 514/410

See application file for complete search history.

(56) References Cited

U.S. PATENT DOCUMENTS

| | | | | |
|---|---|---|---|---|
| 4,910,218 A | * | 3/1990 | Bair | 514/443 |
| 4,999,369 A | * | 3/1991 | Bair | 514/410 |
| 5,523,297 A | | 6/1996 | Pruzanski et al. | |
| 6,872,743 B2 | * | 3/2005 | Beight et al. | 514/410 |

FOREIGN PATENT DOCUMENTS

| | | |
|---|---|---|
| EP | 0 950 661 | 10/1999 |
| WO | WO 00/07590 | 2/2000 |

OTHER PUBLICATIONS

Chemical Abstracts, vol. 124, No. 23 (1996); Columbus, Ohio, US; Abstract No. 317028x, p. 1205; XP002202619.

* cited by examiner

*Primary Examiner*—Golam M. M. Shameem
(74) *Attorney, Agent, or Firm*—Francis O. Ginah

(57) ABSTRACT

A novel class of tetracyclic compounds is disclosed together with the use of such compounds for inhibiting sPLA2 mediated release of fatty acids for treatment of Inflammatory Diseases such as septic shock.

19 Claims, No Drawings

SPLA₂ INHIBITORS

This invention relates to novel tetracyclic compounds useful for Inflammatory Diseases.

The structure and physical properties of human non-pancreatic secretory phospholipase A₂ (hereinafter called, "sPLA₂") has been thoroughly described in two articles, namely, "Cloning and Recombinant Expression of Phospholipase A₂ Present in Rheumatoid Arthritic Synovial Fluid" by Seilhamer, Jeffrey J.; Pruzanski, Waldemar; Vadas Peter; Plant, Shelley; Miller, Judy A Kloss, Jean; and Johnson, Lorin K *The Journal of Biological Chemistry*, Vol. 264, No. 10, Issue of April 5, pp. 5335–5338, 1989; and "Structure and Properties of a Human Non-pancreatic Phospholipase A₂" by Kramer, Ruth M Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid). Such compounds would be of value in the general treatment of conditions induced and/or maintained by overproduction of sPLA₂; such as sepsis or rheumatoid arthritis.

It is desirable to develop new compounds and treatments for sPLA₂ induced diseases.

The present invention relates to a compound of formula (I) and pharmaceutically acceptable salt, solvate or prodrug thereof, useful for the treatment or prevention of inflammatory diseases:

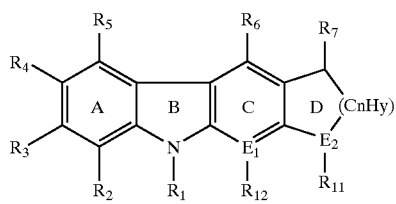

(I)

Wherein;

$E_1$ is C, or N, S with the appropriate number of hydrogen atoms or non-interfering substituents; $E_2$ is C, N or S with the appropriate number of hydrogen atoms or non-interfering groups appended where applicable or $E_2$ is oxygen wherein $R_{11}$ is non-existent;

n is 1, 2 or 3 and y is an appropriate number of hydrogen atoms based on the value of (n) and also based on ring unsaturation;

$R_1$ is selected from group (a), (b), or (c)

wherein;

(a) is $(C_7-C_{20})$alkyl, $(C_7-C_{20})$haloalkyl, $(C_7-C_{20})$alkenyl, $(C_7-C_{20})$alkynyl, carbocyclic radical, or heterocyclic radical, or (b) is a member of (a) substituted with one or more independently selected non-interfering substituents;

(c) is the group —(L)—$R_{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$, $R_3$, and $R_4$ are independently hydrogen, or a group containing 1 to 10 non-hydrogen atoms plus any required hydrogen atoms;

$R_5$ is —$(L_5)$—Z, where —$(L_5)$— is a divalent linker group selected from a bond, or a divalent group selected from:

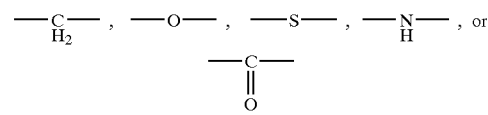

and Z is selected from an amide, thioamide, oxime amide, oxime thioamide, glyoxylamide, hydrazide, ureido or acetamide group represented by the formulae,

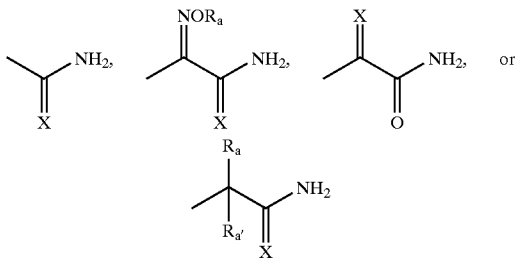

wherein X is oxygen or sulfur, $R_a$ and $R_{a'}$ are independently selected from hydrogen, $(C_1-C_8)$alkyl, aryl, $(C_1-C_8)$alkaryl, $(C_1-C_8)$alkoxy, aralkyl and —CN;

$R_6$ is the group, hydrogen, CONH₂, CONHR$^{6b}$ or —(La)—(acidic group) wherein —$(L_a)$—, is an acid linker having an acid linker length of 1 to 8;

or the group —$(L_h)$—(N-hydroxyfunctional amide group); wherein —$(L_h)$—, is an N-hydroxyfunctional amide linker having a N-hydroxyfunctional amide linker length of 1 to 8; and wherein a N-hydroxyfunctional amide group is represented by the formula:

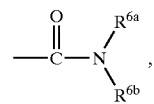

wherein $R^{6a}$ is selected from the group consisting of OH, $(C_1-C_6)$alkoxy, and aryloxy; and wherein $R^{6b}$ is hydrogen or an organic substituent selected from the group consisting of $(C_1-C_8)$alkyl, aryl, $(C_7-C_{14})$aralkyl, $(C_7-C_{14})$alkaryl, $(C_3-C_8)$cycloalkyl, $(C_1-C_8)$alkoxyalkyl and these groups substituted with halogen, —CF₃, —OH, $(C_1-C_8)$alkyl, amino, carbonyl, and —CN;

or $R_6$ is the group —(Lc)—(acylamino acid group)— wherein the "acylamino acid group" is represented by the formula:

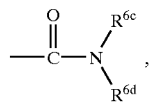

wherein R$^{6c}$ is selected from the group consisting of H, (C$_1$–C$_6$)alkyl, (C$_1$–C$_6$)alkoxy, heteroaryl and aryl, —CF$_3$; and wherein NR$^{6d}$ is an amino acid residue of either a natural or unnatural amino acid with the nitrogen atom being part of the amino group of the amino acid.

R$_7$ is selected from hydrogen, a non-interfering substituent, the group —(L$_h$)—(N-hydroxyfunctional amide group), or the group —(L$_c$)-acylamino acid group), or the group, —(L$_a$)—(acidic group); wherein —(L$_a$)—, is an acid linker having an acid linker length of 1 to 8;

R$_{11}$ is hydrogen or non-existent; R$_{12}$ is hydrogen, C$_1$–C$_4$ alkyl or non-existent, where the corresponding E$_1$ or E$_2$ is independently a nitrogen atom where the valency on nitrogen would be exceeded. When E$_2$ is oxygen R$_{11}$ is non-existent.

The present invention provides novel tetracyclic compounds of formula I having potent and selective effectiveness as inhibitors of mammalian sPLA$_2$.

The present invention also relates to the use of novel tetracyclic compounds of formula I useful in the treatment and/or prevention of Inflammatory Diseases.

This invention also relates to the use of a novel tetracyclic compound of formula I to inhibit mammalian sPLA$_2$ mediated release of fatty acids.

The present invention provides a pharmaceutical composition containing any of the tetracyclic compounds of the invention.

The present invention also relates to the use of a formulation comprising a compound of formula 1, and a carrier or diluent for the treatment or prevention of sepsis.

The present invention relates to the use of a pharmaceutical composition comprising a therapeutically effective amount of SPLA$_2$ inhibitor compounds of formula I and mixtures thereof for the manufacture of a medicament for the treatment of Inflammatory Diseases.

I. Definitions:

The terms, "mammal" and "mammalian" include human and domesticated quadrupeds.

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

The term, "tetracyclic", or "tetracyclic nucleus" as used herein refers to a nucleus (having numbered positions) with the structural formula (X):

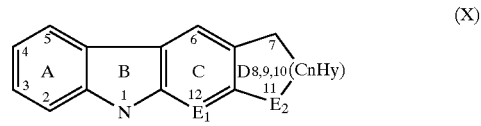

(X)

wherein, n is 1, 2 or 3, and y is the appropriate number of hydrogen atoms depending on D ring unsaturation;

wherein E$_1$ and E$_2$ are independently C, N or S with the appropriate number of hydrogen atoms or other non-interfering substituents appended or E$_2$ is oxygen;

and the letters A, B, C and D are ring identifiers; and wherein, the D ring has zero, single or multiple unsaturation as chemically possible based on ring size and conjugational or electronic effects. The tetracyclic compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic nuclei having 4 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo (1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, dibenzylyl and related dibenzylyl homologues represented by the formula (a):

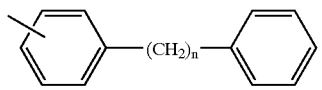

(a)

where n is a number from 1 to 8.

The terms, "non-interfering substituent", or "non-interfering groups" refer to radicals suitable for substitution at positions 1, 2, 3, 4, 7, 8, 9 and/or 10 of the tetracyclic nucleus and on other nucleus substituents (as hereinafter described for Formula I), and radicals suitable for substitution on the heterocyclic radical and carbocyclic radical as defined above. Illustrative non-interfering radicals are $(C_1-C_8)$alkyl, $(C_2-C_8)$alkenyl, $(C_2-C_8)$alkynyl, $(C_7-C_{12})$aralkyl, $(C_7-C_{12})$alkaryl, $(C_3-C_8)$cycloalkyl, $(C_3-C_8)$cycloalkenyl, phenyl, toluyl, xylenyl, biphenyl, $(C_1-C_8)$alkoxy, $(C_2-C_8)$alkenyloxy, $(C_2-C_8)$alkynyloxy, $(C_2-C_{12})$alkoxyalkyl, $(C_2-C_{12})$alkoxyalkyloxy, $(C_2-C_{12})$alkylcarbonyl, $(C_2-C_{12})$alkylcarbonylamino, $(C_2-C_{12})$alkoxyamino, $(C_2-C_{12})$alkoxyaminocarbonyl, $(C_1-C_{12})$alkylamino, $(C_1-C_6)$alkylthio, $(C_2-C_{12})$alkylthiocarbonyl, $(C_1-C_8)$alkylsulfinyl, $(C_1-C_8)$alkylsulfonyl, $(C_2-C_8)$haloalkoxy, $(C_2-C_8)$haloalkylsulfonyl, $(C_2-C_8)$haloalkyl, $(C_2-C_8)$hydroxyalkyl, —C(O)O(($C_2-C_8$)alkyl), —(CH$_2$)$_n$—O—($C_1-C_8$)alkyl, benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8 and R is $(C_1-C_8)$alkyl.

The term, "organic substituent" refers to a monovalent radical consisting of carbon and hydrogen with or without oxygen, nitrogen, sulfur, halogen, or other elements. Illustrative organic substituents are $(C_1-C_8)$alkyl, aryl, $(C_7-C_{14})$aralkyl, $(C_7-C_{14})$alkaryl, $(C_3-C_8)$cycloalkyl, $(C_1-C_8)$alkoxyalkyl and these groups substituted with halogen, —CF$_3$, —OH, $(C_2-C_8)$alkyl, amino, carbonyl, and —CN.

The term "substituted group" is an organic group substituted with one or more non-interfering substituents.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the tetracyclic nucleus have been drawn to show the first line as a connecting bond only. Thus, the group

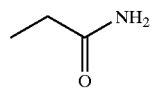

indicates the acetamide radical not the propanamide radical unless otherwise indicated.

The term, "N-hydroxyfunctional amide group" is represented by the formula:

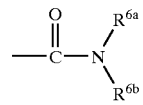

wherein $R^{6a}$ is selected from the group consisting of OH, $(C_1-C_6)$alkoxy, and aryloxy; and wherein $R^{6b}$ is hydrogen or an organic substituent selected from the group consisting of $(C_1-C_8)$alkyl, aryl, $(C_7-C_{14})$aralkyl, $(C_7-C_{14})$alkaryl, $(C_3-C_8)$cycloalkyl, $(C_3-C_8)$alkoxyalkyl and these groups substituted with halogen, —CF$_3$, —OH, $(C_1-C_8)$alkyl, amino, carbonyl, and —CN.

The phrase, "N-hydroxyfunctional amide linker" refers to a divalent linking group symbolized as, —(L$_h$)—, which has the function of joining the 6- or 7-position of the tetracyclic nucleus to an N-hydroxyfunctional amide group in the general relationship:

The words, "hydroxyfunctional amide linker length", refer to the number of atoms (excluding hydrogen) in the shortest chain of the linking group —(L$_h$)— that connects the (6) or (7) position of the tetracyclic nucleus with the N-hydroxyfunctional amide group. The presence of a carbocyclic ring in —(L$_h$)— counts as the number of atoms approximately equivalent to the calculated diameter of the carbocyclic ring. Thus, a benzene or cyclohexane ring in the acid linker counts as 2 atoms in calculating the length of —(L$_h$)—. Illustrative "N-hydroxyfunctional amide linker" groups are;

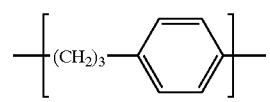

(a)

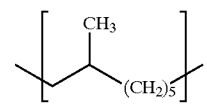

(b)

-continued

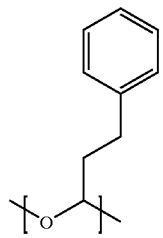
(c)

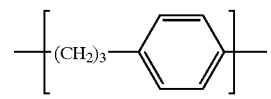
(a)

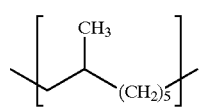
(b)

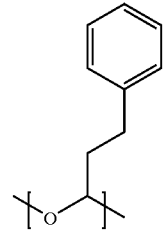
(c)

wherein, groups (a), (b) and (c) have acid linker lengths of 5, 7, and 2, respectively.

The term, "(acidic group)" means an organic group which when attached to a tetracyclic nucleus at the 6 or 7 position, through suitable linking atoms (hereinafter defined as the "acid linker"), acts as a proton donor capable of hydrogen bonding. Illustrative the following:

-5-tetrazolyl,
—SO$_3$H,

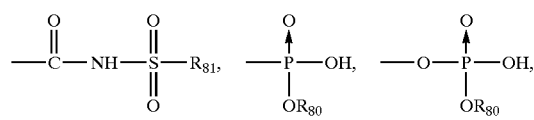

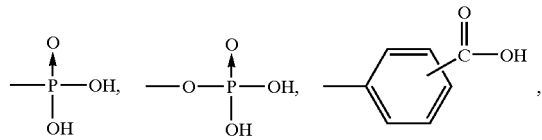

where n is 1 to 8, $R_{80}$ is a metal or ($C_1$–$C_8$) and $R_{81}$ is an organic substituent or —CF$_3$.

The words, "acid linker" refer to a divalent linking group symbolized as, —($L_a$)—, which has the function of joining the (6) or (7) position of the tetracyclic nucleus to an acidic group in the general relationship:

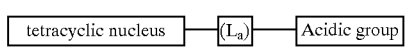

The words, "acid linker length", refer to the number of atoms (excluding hydrogen) in the shortest chain of the linking group —($L_a$)— that connects the 6 or 7 position of the tetracyclic nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative, acid linker groups include;

wherein, groups (a), (b), and (c) have acid linker lengths of 5, 7, and 2, respectively.

The term, "acylamino acid group" is represented by the formula:

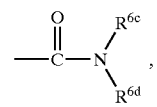

wherein $R^{6c}$ is selected from the group consisting of H, ($C_1$–$C_6$)alkyl, ($C_1$–$C_6$)alkoxy, heteroaryl and aryl, —CF$_3$;

and wherein NR$^{6d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cysteine, glutamine, glutamic acid, histidine, lysine, methionine, serine, threonine, tryptophan, tyrosine and derivatives thereof. Contemplated within the definition of amino acid are 1-proline, d-proline and derivatives thereof. Also contemplated within the definition of amino acids are peptides, polypeptides and derivatives thereof.

The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

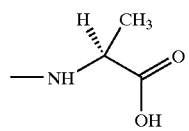

The words, "acylamino acid linker" refer to a divalent linking group symbolized as, —($L_c$)—, which has the function of joining the 6 or 7-position of the tetracyclic nucleus to an acylamino acid group in the general relationship:

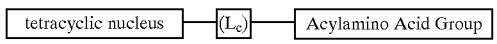

The words, "acylamino acid linker length", refer to the number of atoms (excluding hydrogen) in the shortest chain of the linking group —($L_c$)— that connects the 6- or 7-position of the tetracyclic nucleus with the acylamino acid group. The presence of a carbocyclic ring in —($L_c$)- counts as the number of atoms approximately equivalent to the calculated diameter of the carbocyclic ring. Thus, a benzene or cyclohexane ring in the acid linker counts as 2 atoms in calculating the length of —($L_c$)—.

Illustrative "acylamino acid linker groups" include:

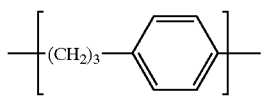

(a)

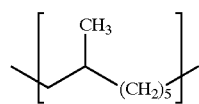

(b)

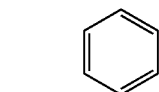

(c)

wherein, groups (a), (b) and (c) have acid linker lengths of 5, 7, and 2, respectively.

The term, "amine", includes primary, secondary and tertiary amines.

The term, "alkylene chain of 1 or 2 carbon atoms" refers to the divalent radicals, —$CH_2$—$CH_2$— and —$CH_2$—.

The term, "group containing 1 to 10 non-hydrogen atoms" refers to relatively small groups which form substituents at the 2-position of the tetracyclic nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —$CF_3$, —Cl, —Br, —$NO_2$, —CN, —$SO_3$; and (ii) groups having hydrogen atoms which contain less than 4 non-hydrogen atoms such as —$CH_3$, —$C_2H_5$, and —CH=$CH_2$.

The term "oxime amide" means the radical, —C(=NOR)—C(O)$NH_2$

The term "thio-oxime amide" means the radical —C(=NOR)—C(S)—$NH_2$.

The term "spiro[5.5]undecanyl" refers to the group represented by the formula;

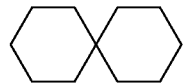

II. The Tetracyclic Compounds of the Invention:

The present invention provides a novel class of tetracyclic compounds useful as $sPLA_2$ inhibitors for the treatment and/or prophylaxis of inflammation attendant to inflammatory diseases. Subclasses of tetracyclic compounds of this invention include tetracyclic oxyacid derivatives, tetracyclic-5-oxime amide oxyacid derivatives, tetracyclic-5-acetamide oxyacid derivatives, tetracyclic-5-glyoxylamide-N-hydroxyfunctional amide derivatives, tetracyclic-5-oxime amide-N-hydroxyfunctional amide derivatives, tetracyclic-5-acetamide hydroxy functional amide derivatives, tetracyclic-5-glyoxylamide acylamino acid derivatives, tetracyclic-5-oxime amide acylamino acid derivatives, tetracyclic-5-acetamide acylamino acid derivatives.

The compounds of the invention are represented by the general formula (I) and include a pharmaceutically acceptable salt, solvate or prodrug thereof;

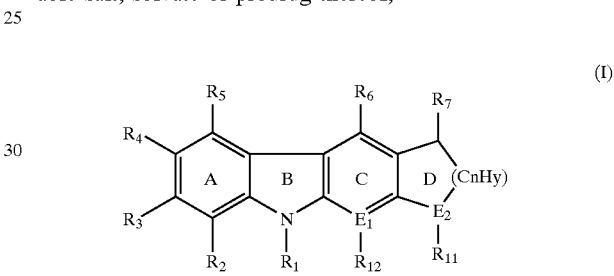

(I)

wherein $E_1$ and $E_2$ are independently C, N, or S with the appropriate number of hydrogen atoms or non-interfering groups appended where applicable;

$E_2$ is also independently oxygen wherein $R_{11}$ is non-existent;

n is 1, 2 or 3 and y is an appropriate number of hydrogen atoms based on the value of n and also based on ring unsaturation;

$R_1$ is selected from group (a), (b), or (c)

wherein;

(a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or (b) is a member of (a) substituted with one or more independently selected non-interfering substituents;

(c) is the group -(L)-$R_{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$, $R_3$, and $R_4$ are independently hydrogen, or a group containing 1 to 10 non-hydrogen atoms plus any required hydrogen atoms;

$R_5$ is —($L_5$)—Z, where —($L_5$)— is a divalent linker group selected from a bond, or a divalent group selected from:

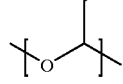

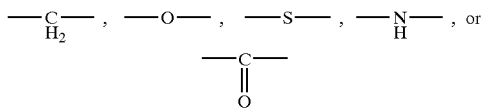

and Z is selected from an amide, thioamide, oximeamide, oximethioamide, glyoxylamide, hydrazide, or acetamide group represented by the formulae,

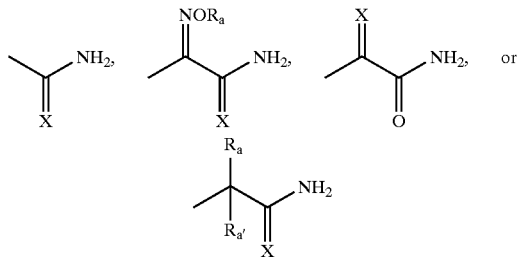

wherein X is oxygen or sulfur, $R_a$ and $R_{a'}$ are independently selected from hydrogen, $(C_1-C_8)$alkyl, aryl, $(C_1-C_8)$alkaryl, $(C_1-C_8)$alkoxy, aralkyl and —CN;

$R_6$ is the group, hydrogen, $CONH_2$, $CONHR^{6b}$ or —$(L_a)$—(acidic group) wherein —$(L_a)$—, is an acid linker having an acid linker length of 1 to 8;

or the group —$(L_h)$—(N-hydroxyfunctional amide group); wherein —$(L_h)$—, is an N-hydroxyfunctional amide linker having a N-hydroxyfunctional amide linker length of 1 to 8; and wherein a N-hydroxyfunctional amide group is represented by the formula:

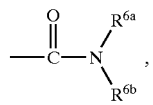

wherein Y is oxygen;

$R^{6a}$ is selected from the group consisting of OH, $(C_1-C_6)$ alkoxy, and aryloxy; and wherein $R^{6b}$ is hydrogen or an organic substituent selected from the group consisting of $(C_1-C_8)$alkyl, aryl, $(C_7-C_{14})$ aralkyl, $(C_7-C_{14})$alkaryl, $(C_3-C_8)$cycloalkyl, $(C_1-C_8)$ alkoxyalkyl and these groups substituted with halogen, —$CF_3$, —OH, $(C_1-C_8)$alkyl, amino, carbonyl, and —CN;

or $R_6$ is the group —(Lc)—(acylamino acid group)— wherein the "acylamino acid group" is represented by the formula:

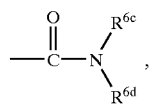

wherein $R^{6c}$ is selected from the group consisting of H, $(C_1-C_6)$alkyl, $(C_1-C_6)$alkoxy, heteroaryl and aryl, —$CF_3$; and wherein $NR^{6d}$ is an amino acid residue of either a natural or unnatural amino acid with the nitrogen atom being part of the amino group of the amino acid.

$R_7$ is selected from hydrogen, a non-interfering substituent, the group —$(L_h)$—(N-hydroxyfunctional amide group), or the group —$(L_c)$-acylamino acid group), or the group, —$(L_a)$—(acidic group); wherein —$(L_a)$—, is an acid linker having an acid linker length of 1 to 8; and provided that at least one of $R_6$ or $R_7$ is the group —$(L_h)$—(N-hydroxyfunctional amide group), or the group —$(L_c)$-acylamino acid group), or the group, —$(L_a)$—(acidic group).

$R_{11}$ and $R_{12}$ are non-existent where the corresponding $E_1$ or $E_2$ is independently a nitrogen atom and where the valency on nitrogen would be exceeded. $R_{11}$ is also non-existent when $E_2$ is oxygen.

For positions 1 through 12 as shown in structure (X), and in compounds of the invention, it should be understood that where valency is incomplete an extra bond to hydrogen is contemplated by this invention to effect complete valency for the particular carbon, nitrogen or sulfur at that position of the ring i.e. D ring.

Preferred Subgroups of Compounds of Formula (I):

A preferred subclass of compounds of formula I are those wherein $E_1$ and $E_2$ are independently carbon.

Another preferred class of compounds of formula I are those wherein $E_1$ and $E_2$ are independently nitrogen.

Also preferred is a subclass of compound I wherein $E_2$ is sulfur.

Another preferred subclass are compounds of formula I wherein the D ring is a 5 or 6 membered ring.

Also preferred is a subclass of compounds of formula I wherein the D ring is benzene. Also preferred is a subclass wherein the C and D rings combine to form a naphthalene ring system.

Preferred $R_1$ Substituents:

A preferred subclass of compounds of formula (I) are those where for $R_1$ the divalent linking group —$(L_1)$— is a group represented by any one of the following formulae (Ia), (Ib), (Ic), (Id), (Ie), or

(Ia)

(Ib)

(Ic)

(Id)

(Ie)

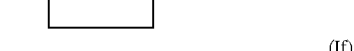 or

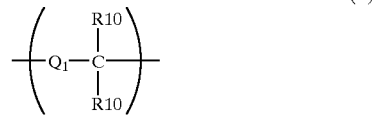

(If)

where $Q_1$ is a bond or any of the divalent groups (Ia), (Ib), (Ic), (Id), (Ie), and (If) and each $R_{10}$ is independently hydrogen, $(C_1-C_8)$alkyl, $(C_1-C_8)$haloalkyl or $(C_1-C_8)$ alkoxy.

Particularly preferred as the linking group —(L$_1$)— of R$_1$ is an alkylene chain of 1 or 2 carbon atoms, namely, —(CH$_2$)— or —(CH$_2$—CH$_2$)—.

The preferred group for R$_{11a}$ is a substituted or unsubstituted group selected from the group consisting of (C$_5$–C$_{14}$)cycloalkyl, (C$_5$–C$_{14}$)cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a);

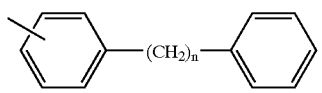
(a)

where n is a number from 1 to 8.

Particularly preferred are compounds wherein for R$_1$ the combined group —(L$_1$)—R$_{11a}$ is selected from the group consisting of

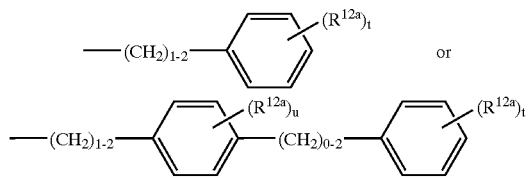

where R$^{12a}$ is a radical independently selected from halo, (C$_1$–C$_8$)alkyl, (C$_1$–C$_8$)alkoxy, —S—((C$_1$–C$_8$)alkyl), —O—((C$_1$–C$_8$)alkyl) and (C$_1$–C$_8$)haloalkyl where t is a number from 0 to 5 and u is a number from 0 to 4.

is the group —(L$_1$)—R$_{11a}$; where, —(L$_1$)— is a divalent linking group of 1 to 8 atoms and where R$_{11a}$ is a group selected from (a) or (b).

Preferred for R$_{11a}$ is —(CH$_2$)m-R$^{12a}$ wherein m is an integer from 1 to 6, and R$^{12a}$ is (d) a group represented by the formula:

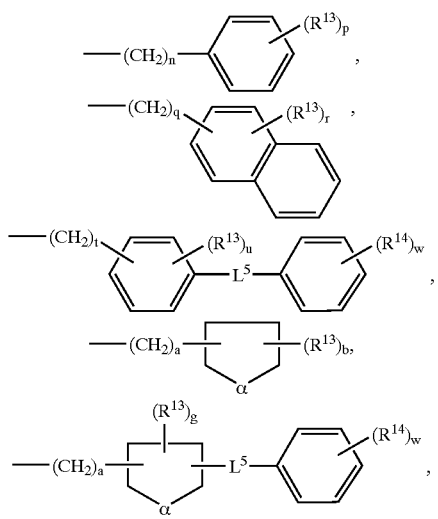

-continued

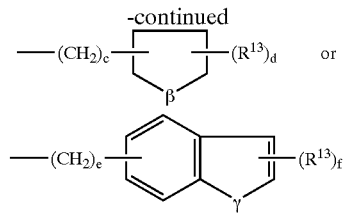

wherein a, c, e, n, q, and t are independently an integer from 0 to 2, R$^{13}$ and R$^{14}$ are independently selected from a halogen, C$_1$ to C$_8$ alkyl, C$_1$ to C$_8$ alkyloxy, C$_1$ to C$_8$ alkylthio, aryl, heteroaryl, and C$_1$ to C$_8$ haloalkyl, α is an oxygen atom or a sulfur atom, L$^5$ is a bond, —(CH$_2$)v—, —C=C—, —CC—, —O—, or —S—, v is an integer from 0 to 2, β is —CH$_2$— or —(CH$_2$)$_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of (C$_1$ to C$_6$)alkyl, (C$_1$ to C$_8$)alkyloxy, (C$_1$ to C$_8$)haloalkyloxy, (C$_1$ to C$_8$)haloalkyl, aryl, and a halogen.

Preferred R$_2$ Substituents:

When E$_1$ is a carbon atom, R$_2$ is preferably selected from the group consisting of hydrogen, (C$_1$–C$_4$)alkyl, (C$_2$–C$_4$) alkenyl, —O—((C$_1$–C$_4$)alkyl), —S—((C$_1$–C$_3$)alkyl), —(C$_3$–C$_4$)cycloalkyl, —CF$_3$, halo, —NO$_2$, —CN, —SO$_3$. Particularly preferred R$_2$ groups are selected from hydrogen, methyl, ethyl, propyl, isopropyl, cyclopropyl, —F, —CF$_3$, —Cl, —Br, or —O—CH$_3$.

Preferred R$_3$/R$_4$ Substituents:

R$_3$ and R$_4$ are independently selected preferably from the group consisting of hydrogen, (C$_1$–C$_4$)alkyl, (C$_2$–C$_4$)alkenyl, —O—((C$_1$–C$_4$)alkyl), —S—((C$_1$–C$_3$)alkyl), —(C$_3$–C$_4$)cycloalkyl —CF$_3$, halo, —NO$_2$, —CN, —SO$_3$. Particularly preferred R$_3$ and R$_4$ groups are independently selected from hydrogen, methyl, ethyl, propyl, isopropyl, cyclopropyl, —F, —CF$_3$, —Cl, —Br, or —O—CH$_3$.

Preferred R$_5$ Substituents:

A preferred subclass of compounds of formula (I) are those wherein X is oxygen.

Also preferred is a subclass of compounds of formula I wherein Z is a glyoxylamide (glyoxamide) group represented by

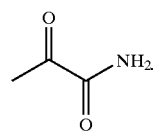

Another preferred subclass of compounds of formula (I) are those wherein Z is an amide group

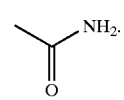

Another preferred subclass of compounds of formula (I) are those wherein Z is an oxime amide group.

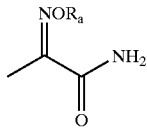

Also preferred are compounds of formula (I) wherein Z is an acetamide group represented by the formulae:

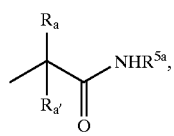

wherein $R_a$ and $R_{a'}$ are independently selected from hydrogen, $(C_1-C_8)$alkyl, aryl, $(C_1-C_8)$alkaryl, $(C_1-C_8)$alkoxy, aralkyl and —CN, and $R^{5a}$ is hydrogen, methyl or ethyl. For the group $R_5$ it is most preferred that the linking group —$(L_5)$— be a bond.

Preferred $R_6$ Substituents:

A preferred subclass of compounds of formula I are those wherein $R_6$ is a substituent selected from hydrogen, $CONH_2$, $CONHR^{6b}$, or the group, —$(L_a)$—(acidic group); wherein —$(L_a)$— is an acid linker; provided the acid linker group, —$(L_a)$— for $R_6$ is selected from the group consisting of;

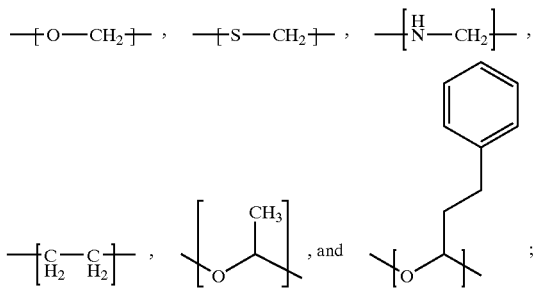

and provided, that at least one of $R_6$ and $R_7$ must be the group, —$(L_a)$—(acidic group) or the group —$(L_h)$—(N-hydroxyfunctional amide group) or the group —$(L_c)$—(acylamino acid group), and wherein the (acidic group) on the group —$(L_a)$—(acidic group) of $R_6$ or $R_7$ is selected from —$CO_2H$, $CO_2Na$, $CO_2R_a$, —$SO_3H$, or —$P(O)(OH)_2$;

Another preferred subclass of compounds of formula I are those wherein $R_6$ is the group —$(Lc)$—(acylamino acid group)-, wherein —$(Lc)$— is an acylamino acid linker with an acylamino acid linker length of 2 or 3, and the "acylamino acid group" is represented by the formula:

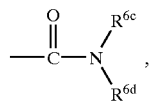

wherein $R^{6c}$ is selected from the group consisting of H, $(C_1-C_6)$alkyl, $(C_1-C_6)$alkoxy, heteroaryl and aryl, —$CF_3$; and wherein $NR^{6d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof.

Another preferred subclass of compounds of formula (I) are those wherein $R_6$ is a substituent having an N-hydroxyfunctional amide linker with an N-hydroxyfunctional amide linker length of 2 or 3 and the N-hydroxyfunctional amide linker group, —$(L_h)$—, for $R_6$ is selected from a group represented by the formula;

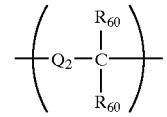

where $Q_2$ is selected from the group —$(CH_2)$—, —O—, —NH—, —C(O)—, and —S—, and each $R_{60}$ is independently selected from hydrogen, $(C_1-C_8)$alkyl, aryl, $(C_1-C_8)$alkaryl, $(C_1-C_8)$alkoxy, aralkyl, and halo.

Most preferred subclasses of compound of formula (I) are compounds where the acid linker —$(La)$—, or the N-hydroxyfunctional amide linker, —$(L_h)$—, or the acylamino acid linker —$(L_c)$—, for $R_6$ is independently selected from the specific groups;

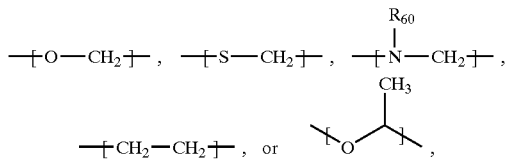

wherein $R_{60}$ is hydrogen or $(C_1-C_8)$alkyl.

Preferred as the N-hydroxyfunctional amide group within the group $R_6$ is the group:

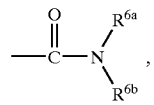

wherein $R^{6a}$ is selected from the group consisting of OH, $(C_1-C_6)$alkoxy and aryloxy; and wherein $R^{6b}$ is an organic substituent selected from the group consisting of H, $(C_1-C_8)$alkyl, aryl, $(C_7-C_{14})$aralkyl, $(C_7-C_{14})$alkaryl, $(C_3-C_8)$cycloalkyl, $(C_1-C_8)$alkoxyalkyl and these groups substituted with halogen, —$CF_3$, —OH, $(C_1-C_8)$alkyl, amino, carbonyl, and —CN. A more preferred $R^{6a}$ group is selected from the group consisting of —OH, —$OCH_3$ and —$OC_2H_5$ while a more preferred $R^{6b}$ is selected from the group consisting of H, $(C_1-C_8)$alkyl, aryl, $(C_7-C_{14})$aralkyl, $(C_7-C_{14})$alkaryl, $(C_3-C_8)$cycloalkyl. A most preferred $R^{6b}$ is a group selected from H, $CH_3$, $C_2H_5$ and $C_3H_7$.

A salt or a prodrug derivative of the (N-hydroxyfunctional amide group) is also a suitable substituent.

Preferred $R_7$ Substituents:

A preferred $R_7$ substituent is the group hydrogen, a non-interfering substituent or the group —(La)—(acidic group) wherein the preferred acid linker, —$(L_a)$—, for $R_7$ is selected from the group consisting of;

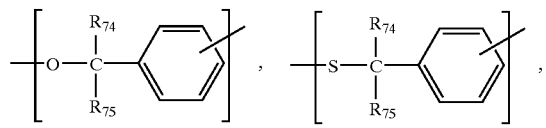

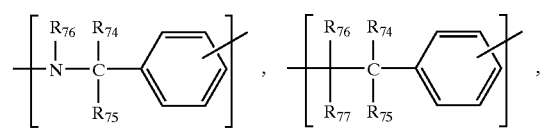

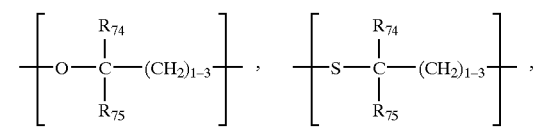

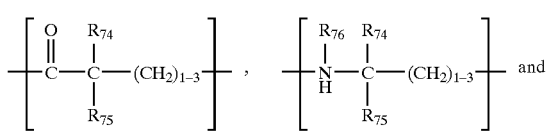

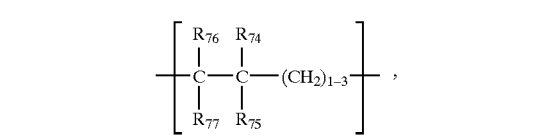

wherein $R_{74}$, $R_{75}$, $R_{76}$ and $R_{77}$ are independently hydrogen, $(C_1-C_8)$alkyl, $(C_1-C_8)$haloalkyl, aryl, $(C_1-C_8)$alkoxy, or halo. Preferred (acidic group) for $R_7$ is selected from the group consisting of —$CO_2H$, —$SO_3H$ and —$P(O)(OH)_2$. Most preferred for $R_7$ is the group hydrogen or a non-interfering substituent.

Most preferred compounds of the invention are those having the general formula (II) or (III) or (IV) or (V) or a pharmaceutically acceptable salt, solvate or prodrug derivative thereof;

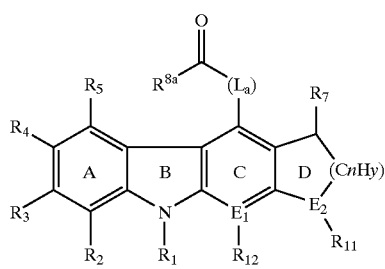

(II)

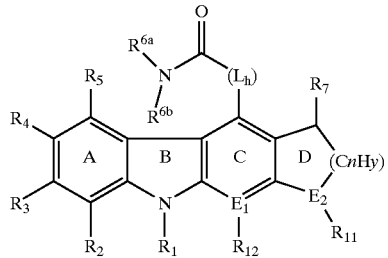

(III)

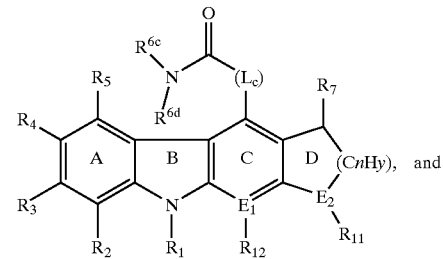

(IV)

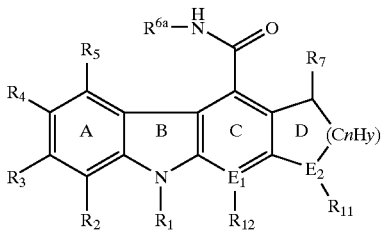

(V)

wherein;

$E_1$ and $E_2$ are independently C, N, S, or O with the appropriate number of hydrogen atoms or non-interfering substituents based on ring size and degree of unsaturation;

$R_1$ is selected from group (a), (b), or (c)

wherein;

(a) is $(C_7-C_{20})$alkyl, $(C_7-C_{20})$haloalkyl, $(C_7-C_{20})$alkenyl, $(C_7-C_{20})$alkynyl, carbocyclic radical, or heterocyclic radical, or (b) is a member of (a) substituted with one or more independently selected non-interfering substituents;

(c) is the group —(L)—$R_{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$, $R_3$, and/or $R_4$ where applicable is selected from hydrogen, methyl, ethyl, propyl, isopropyl, cyclopropyl, —F, —$CF_3$, —Cl, —Br, or —O—$CH_3$;

$R_5$ is —$(L_5)$—Z wherein $(L_5)$ is preferably a bond and Z is selected from the group consisting of

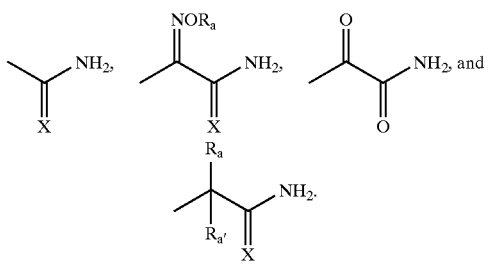

The Acidic Tetracyclic Compounds of the Invention

The acidic group tetracyclic compounds of the Invention are represented by a compound of formula (II) below:

II

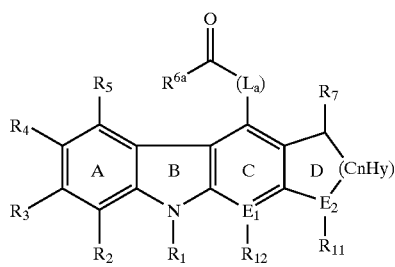

wherein E is carbon 1 or nitrogen; n=1, and
wherein $(L_a)$ is an acid linker having an acid linker length of 2 or 3
$R_1$ is as described previously;
$R_2$ is as described previously;
$R_3$, and $R_4$ are as described previously;
$R_5$ is —$(L_5)$—Z, where —$(L_5)$— is a divalent linker group selected from a bond or a divalent group selected from:

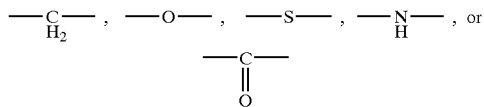

and Z is selected from an amide, thioamide or glyoxylamide, acetamide or thioacetamide, oxime, hydrazide radical (group) represented by the formulae,

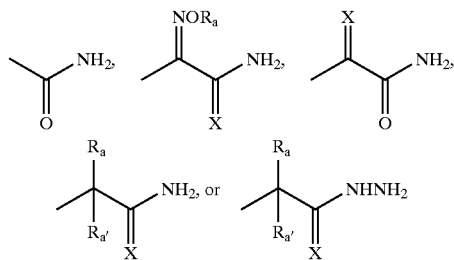

wherein X is oxygen or sulfur, $R_a$ and $R_{a'}$ are independently selected from hydrogen, $(C_1-C_8)$alkyl, aryl, $(C_1-C_8)$alkaryl;

$R_7$ is selected from hydrogen, a non-interfering substituent, or the group, —$(L_a)$—(acidic group);

wherein —$(L_a)$—, is an acid linker having an acid linker length of 1 to 8.

The N-hydroxyfunctional Amide Tetracyclic Compounds of the Invention

The N-hydroxyfunctional amide tetracyclic Compounds of the Invention are represented by the general structure III below:

III

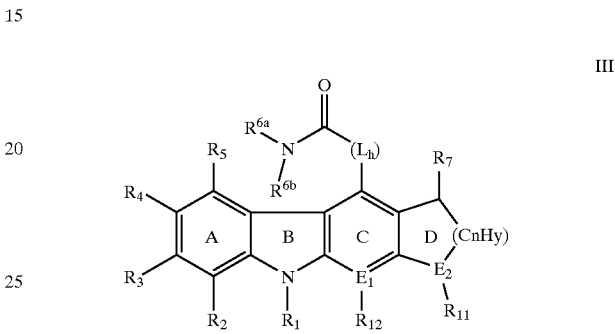

Wherein, $E_1$ and $E_2$ are independently carbon, nitrogen or sulfur with the appropriate number of non-interfering substituents based on D ring size and degree of unsaturation;
$R_1$, $R_2$, $R_3$ and $R_4$ are as described previously;
$R_5$ is —$(L_5)$—Z, where —$(L_5)$— is a divalent linker group selected from a bond or a divalent group selected from:

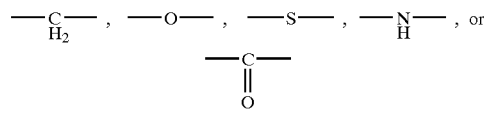

and Z is selected from an amide, thioamide or glyoxylamide, acetamide or thioacetamide, oxime, hydrazide radical (group) represented by the formulae,

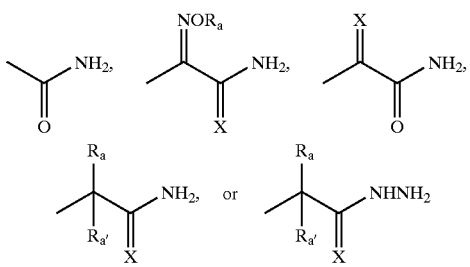

wherein X is oxygen or sulfur, $R_a$ and $R_{a'}$ are independently selected from hydrogen, $(C_1-C_8)$alkyl, aryl, $(C_1-C_8)$alkaryl;

Preferred $R_6$ Substituents:
A preferred subclass of compounds of formula (III) are those wherein $R_6$ is a substituent having N-hydroxyfunctional amide linker with an N-hydroxyfunctional amide linker length of 2 or 3 and the N-hydroxyfunctional amide linker group, —($L_h$)—, for $R_6$ is selected from a group represented by the formula;

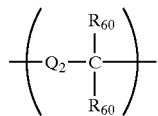

where $Q_2$ is selected from the group —($CH_2$)—, —O—, —NH—, —C(O)—, and —S—, and each $R_{60}$ is independently selected from hydrogen, ($C_1$–$C_8$)alkyl, aryl, ($C_1$–$C_8$)alkaryl, ($C_1$–$C_8$)alkoxy, aralkyl, and halo. Most preferred are compounds where the N-hydroxyfunctional amide linker, —($L_h$)—, for $R_6$ is selected from the specific groups;

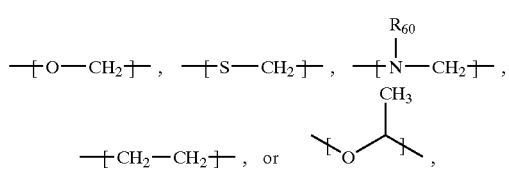

where $R_{60}$ is hydrogen or ($C_1$–$C_8$)alkyl.

Preferred as the (N-hydroxyfunctional amide group) in the group $R_6$ is the group:

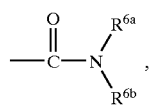

wherein $R^{6a}$ is selected from the group consisting of OH, ($C_1$–$C_6$)alkyl, ($C_1$–$C_6$)alkoxy, heteroaryl and aryl; and wherein, $R^{6b}$ is hydrogen, ($C_1$–$C_6$)alkyl, phenyl and benzyl.

$R_7$ is preferably selected from hydrogen or a non-interfering substituent.

The Acylamino Acid Tetracyclic Compounds of the Invention:

The tetracyclic acylamino acid compounds of the invention are represented by the general formula (IV) or a pharmaceutically acceptable salt, solvate or prodrug thereof;

IV

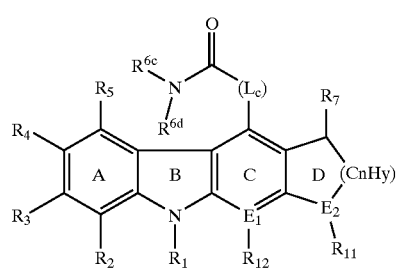

wherein $E_1$ and $E_2$ are independently carbon or nitrogen or sulfur;

$R_1$, $R_2$, $R_3$, and $R_4$ are as described previously;

$R_5$ is —($L_5$)—Z, where —($L_5$)— is a divalent linker group selected from a bond or a divalent group selected from:

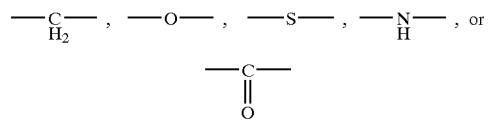

and Z is selected from an amide, thioamide or glyoxylamide, acetamide or thioacetamide, oxime, hydrazide radical (group) represented by the formulae,

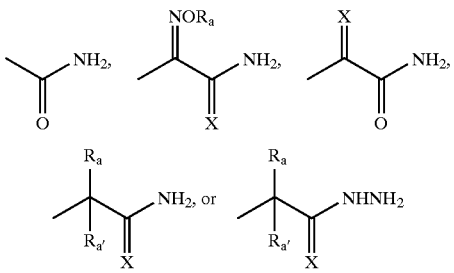

wherein X is oxygen or sulfur, $R_a$ and $R_{a'}$ are independently selected from hydrogen, ($C_1$–$C_8$)alkyl, aryl, ($C_7$–$C_{14}$)alkaryl;

Preferred $R_6$ Substituents:

A preferred subclass of compounds of formula (IV) are those wherein $R_6$ is a substituent having an acylamino acid linker with an acylamino acid linker length of 2 or 3 and the acylamino acid linker group, —($L_c$)—, for $R_6$ is selected from a group represented by the formula;

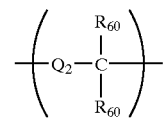

where $Q_2$ is selected from the group —($CH_2$)—, —O—, —NH—, —C(O)—, and —S—, and each $R_{60}$ is independently selected from hydrogen, ($C_1$–$C_8$)alkyl, aryl, ($C_1$–$C_8$)alkaryl, ($C_1$–$C_8$)alkoxy, aralkyl, and halo. Most preferred are compounds where the acylamino acid linker, —($L_c$)—, for $R_6$ is selected from the specific groups;

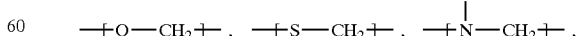
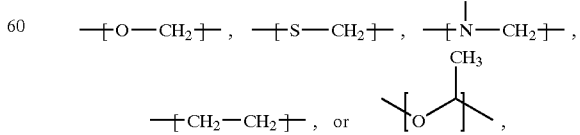

where $R_{60}$ is hydrogen or ($C_1$–$C_8$)alkyl.

Preferred as the (acylamino acid group) for the group $R_6$ is the group:

$$-\overset{O}{\underset{}{C}}-\underset{R^{6d}}{\overset{R^{6c}}{N}},$$

wherein $R^{6c}$ is selected from the group consisting of H, $(C_1-C_6)$alkyl, $(C_1-C_6)$alkoxy, heteroaryl and aryl; and wherein $NR^{6d}$ is an amino acid residue of either a natural or unnatural amino acid with the nitrogen atom being part of the amino group of the amino acid. A preferred $R^{6c}$ group is the group hydrogen (H). A preferred source of amino acid residue is the amino acid group selected from the group comprising isoleucine, valine, phenylalanine, aspartic acid, leucine, glycine and isomers and derivatives thereof. A salt or a prodrug derivative of the (acylamino acid group) is also a suitable substituent.

Particularly preferred are $R^{6d}$ groups that combine with the nitrogen atom to represent amino acid residues from the amino acid groups selected from: glycine, glycine methyl ester, L-alanine, L-alanine methylester, L-leucine, L-leucine methyl ester, L-aspartic acid, L-aspartic acid dimethylester, L-phenyl alanine, L-phenylalanine methyl ester, malonic acid, malonic acid dimethylester, L-valine, L-valine methyl ester, L-isoleucine, L-isoleucine methyl ester, or salt, and derivatives thereof.

$R_7$ is selected from hydrogen, a non-interfering substituent or the group, $-(L_a)-$(acidic group); wherein $-(L_a)-$, is an acid linker having an acid linker length of 1 to 8.

Preferred acylamino acid compounds of the invention are those having the general formula (IVa), or a pharmaceutically acceptable salt, solvate or prodrug derivative thereof;

(IVa)

wherein;

n is 1 or 2; and y is 1, 2 or 4 depending on D ring unsaturation.

$R_1$ is selected from $(C_1-C_8)$alkyl, aryl, and alkylaryl;

$R_2$, $R_3$, and $R_4$ are independently selected from the group consisting of hydrogen, methyl, ethyl, propyl, isopropyl, cyclopropyl, $-F$, $-CF_3$, $-Cl$, $-Br$, or $-O-CH_3$;

$R_5$ is the group $-(L_5)-Z$, wherein Z is selected from the groups amide and hydrazide and wherein $L_5$ is a bond;

and wherein $R^{6c}$ is selected from the group consisting of H, $(C_1-C_6)$alkyl, $(C_1-C_6)$alkoxy, heteroaryl and aryl; and wherein $NR^{6d}$ is an amino acid residue of either a natural or unnatural amino acid with the nitrogen atom being part of the amino group of the amino acid. A preferred $R^{6c}$ group is the group hydrogen (H); and $-(Lc)-$ is a divalent group selected from;

$$-\!\!\left[O-CH_2\right]\!\!-, \quad -\!\!\left[S-CH_2\right]\!\!-.$$

The tetracyclic-5-acetamide sPLA$_2$ inhibitor compounds of the present invention are represented by compounds of formula (V), and pharmaceutically acceptable salts and prodrug derivatives thereof, (V)

wherein;

the D ring has 0 to 2 double bonds and an appropriate number of hydrogen atom or non-interfering group appendages;

$E_1$ and $E_2$ are independently carbon or nitrogen;

$R_2$, $R_3$, and $R_4$ are independently selected from the group consisting of is halo, $(C_1-C_2)$alkylthio, or $(C_1-C_2)$alkoxy;

each $R_a$ and $R_{a'}$ are as described previously;

$R_{16}$ is the group, $-(L_h)-$(N-hydroxyfunctional amide group); wherein $-(L_h)-$, is an N-hydroxyfunctional amide linker having an N-hydroxyfunctional amide linker length of 1 to 8; and wherein a N-hydroxyfunctional amide is represented by the formula:

$$-\overset{O}{\underset{}{C}}-\underset{R^{16b}}{\overset{R^{16a}}{N}},$$

wherein $R^{16a}$ is selected from the group consisting of OH, $(C_1-C_6)$alkoxy, and aryloxy; and wherein $R^{16b}$ is hydrogen or an organic substituent selected from the group consisting of $(C_1-C_8)$alkyl, aryl, $(C_7-C_{14})$aralkyl, $(C_7-C_{14})$alkaryl, $(C_3-C_8)$cycloalkyl, $(C_1-C_8)$alkoxyalkyl and these groups substituted with halogen, $-CF_3$, $-OH$, $(C_1-C_8)$alkyl, amino, carbonyl, and $-CN$; or $R_{16}$ is the group, $-(L_c)-$(acylamino acid group); wherein $-(L_c)-$, is an acylamino acid linker having an acylamino acid linker length of 1 to 8; or $R_{16}$ is the group, $-(L_a)-$(acidic group); wherein $-(L_a)-$, is an acid linker having an acid linker length of 1 to 8;

$R_{17}$ is hydrogen, $(C_1-C_{10})$alkyl, $(C_1-C_{10})$alkenyl, $(C_1-C_{10})$alkynyl, $(C_3-C_8)$cycloalkyl, aryl, aralkyl;

The Tetracyclic-5-amide Compounds

A compound of formula (VI) or a pharmaceutically acceptable salt, solvate or prodrug represent tetracyclic-5-amide compounds of the invention thereof;

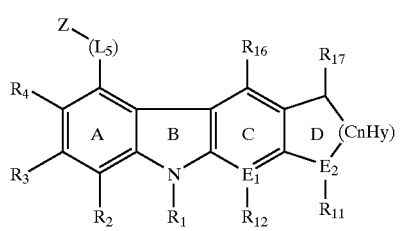

(VI)

wherein;

$R_1$ is as described previously;

$R_2$ is hydrogen, or a group containing 1 to 4 non-hydrogen atoms plus any required hydrogen atoms;

$R_3$ and $R_4$ are independently hydrogen or a non-interfering group;

—($L_5$)—Z, is the group where —($L_5$)— is a divalent linker group selected from a bond or a divalent group selected from:

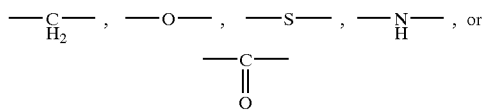

and Z is selected from an amide or thioamide radical or group represented by the formulae,

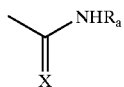

wherein, X is oxygen or sulfur; and $R_a$ is selected from hydrogen, ($C_1$–$C_8$)alkyl, aryl, ($C_1$–$C_8$)alkaryl;

$R_{11}$ and $R_{12}$ are as described previously;

$R_{16}$ is the group, —($L_a$)—(acidic group); wherein —($L_a$)—, is an acid linker having an acid linker length of 1 to 8, or the group —($L_h$)—(N-hydroxyfunctional amide group); wherein —($L_h$)—, is an N-hydroxyfunctional amide linker having an N-hydroxyfunctional amide linker length of 1 to 8; or the group —($L_c$)—(acylamino acid group); wherein —($L_c$)— is an acylamino acid linker having an acylamino acid linker length of 1 to 8.

$R_{17}$ is selected from hydrogen, a non-interfering substituent, or the group, —($L_a$)—(acidic group); wherein —($L_a$)—, is an acid linker having an acid linker length of 1 to 8; or $R_{17}$ is selected from hydrogen, non-interfering substituent, carbocyclic radical, carbocyclic radical substituted with non-interfering substituent(s), heterocyclic radicals, and heterocyclic radical substituted with non-interfering substituent(s).

$R_{18}$ is selected from hydrogen, non-interfering substituent, carbocyclic radical, carbocyclic radical substituted with non-interfering substituent(s), heterocyclic radicals, and heterocyclic radical substituted with non-interfering substituent(s).

The Tetracyclic-5-glyoxylamide Compounds

Compounds of formula (VII) or a pharmaceutically acceptable salt, solvate or prodrug represent tetracyclic-5-glyoxylamide compounds of the invention thereof;

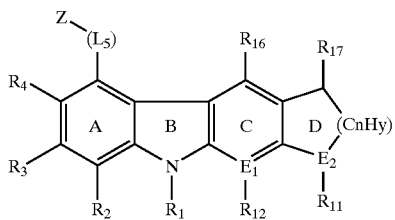

(VII)

wherein $E_1$ and $E_2$ are independently C or N;

$R_2$ is hydrogen, or a group containing 1 to 4 non-hydrogen atoms plus any required hydrogen atoms;

$R_3$ and $R_4$ is each independently selected from hydrogen or a non-interfering group;

—($L_5$)—Z, is the group where —($L_5$)— is a divalent linker group selected from a bond or a divalent group selected from:

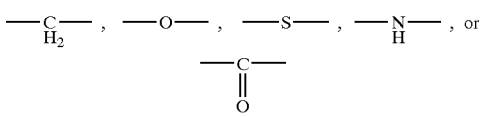

and Z is a glyoxylamide group represented by the formulae,

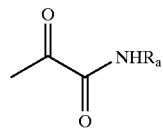

wherein, $R_a$ is selected from hydrogen, ($C_1$–$C_8$)alkyl, aryl, ($C_1$–$C_8$)alkaryl, and aralkyl; and wherein a most preferred $R_a$ is hydrogen;

$R_{11}$ is as described previously;

$R_{16}$ is the group, —($L_a$)—(acidic group); wherein —($L_a$)—, is an acid linker having an acid linker length of 1 to 8, or the group —($L_h$)—(N-hydroxyfunctional amide group); wherein —($L_h$)—, is an N-hydroxyfunctional amide linker having an N-hydroxyfunctional amide linker length of 1 to 8; or the group —($L_c$)—(acylamino acid group); wherein —($L_c$)—, is an acylamino acid linker having an acylamino acid linker length of 1 to 8;

$R_{17}$ is selected from hydrogen, a non-interfering substituent, or the group, —($L_a$)—(acidic group); wherein —($L_a$)—, is an acid linker having an acid linker length of 1 to 8;

$R_{18}$ and $R_{19}$ are independently selected from hydrogen, non-interfering substituent, carbocyclic radical, carbocyclic radical substituted with non-interfering substituent(s), heterocyclic radicals, and heterocyclic radical substituted with non-interfering substituent(s).

The Tetracyclic-5-oxime Amide Compounds

Compounds of formula (VIII) or a pharmaceutically acceptable salt, solvate or prodrug represent tetracyclic-5-oxime amide compounds of the invention thereof;

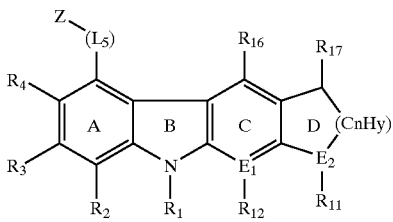

(VIII)

wherein;

$E_1$ and $E_2$ are independently C or N or S, or O with the appropriate number of non-interfering groups appended depending on ring saturation;

$R_{11}$ is as described previously;

$R_{12}$ is hydrogen, or a group containing 1 to 4 non-hydrogen atoms plus any required hydrogen atoms;

$R_3$ and $R_4$ are independently a non-interfering group;

—($L_5$)—Z, is the group where —($L_5$)— is a divalent linker group selected from a bond or a divalent group selected from:

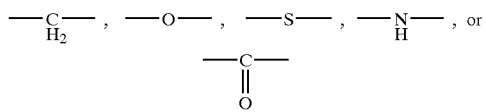

and Z is selected from an oxime amide group represented by the formulae,

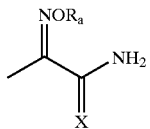

wherein, X is oxygen or sulfur; and $R_a$ is selected from hydrogen, ($C_1$–$C_8$)alkyl, aryl, ($C_1$–$C_8$)alkaryl, ($C_1$–$C_8$) alkoxy, aralkyl and —CN;

$R_{16}$ is the group, hydrogen, or the group —($L_a$)—(acidic group); wherein —($L_a$)—, is an acid linker having an acid linker length of 1 to 8, or the group —($L_h$)—(N-hydroxyfunctional amide group); wherein —($L_h$)—, is an N-hydroxyfunctional amide linker having an N-hydroxyfunctional amide linker length of 1 to 8; or the group —($L_c$)— (acylamino acid group); wherein —($L_c$)— is acylamino acid linker having an acylamino acid linker length of 1 to 8;

$R_{17}$ is selected from hydrogen, a non-interfering substituent, or the group, —($L_a$)—(acidic group); wherein —($L_a$)—, is an acid linker having an acid linker length of 1 to 8.

$R_{18}$, and $R_{19}$ are selected from hydrogen, non-interfering substituent, carbocyclic radical, carbocyclic radical substituted with non-interfering substituent(s), heterocyclic radicals, and heterocyclic radical substituted with non-interfering substituent(s).

Most preferred compounds (and all pharmaceutically acceptable salts, solvates and prodrug derivatives thereof) which are illustrative of the compounds of the invention for treatment of a human afflicted with Inflammatory Disease, a pharmaceutically acceptable salt, solvate, or a prodrug derivative of a compound selected from the group consisting of:

(10-Benzyl-6-carbamoyl-1,2,3,10-tetrahydrocyclopenta[a] carbazol-5-yloxy)acetic acid methyl ester;

(10-Benzyl-6-carbamoyl-1,2,3,10-tetrahydrocyclopenta[a] carbazol-5-yloxy)acetic acid;

(11-Benzyl-7-carbamoyl-2,3,4,11-tetrahydro-1H-benzo[a] carbazol-6-yloxy)acetic acid methyl ester, and (11-Benzyl-7-carbamoyl-2,3,4,11-tetrahydro-1H-benzo[a] carbazol-6-yloxy)acetic acid;

(5-Benzyl-1-carbamoyl-5H-benzo[b]carbazol-11-yloxy)-acetic acid, sodium salt; and (5-Benzyl-1-carbamoyl-5H-benzo[b]carbazol-11-yloxy)-acetic acid, methyl ester;

Preferred compounds of the invention are represented by the formulae (C1), (C2), (C3), (C4), (C5), (C6), (C7), or (C8);

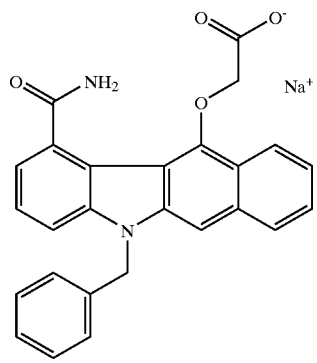

(C1)

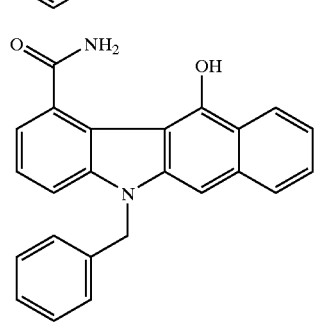

(C2)

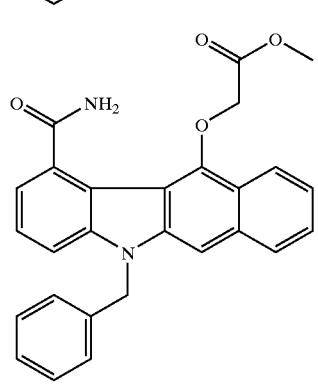

(C3)

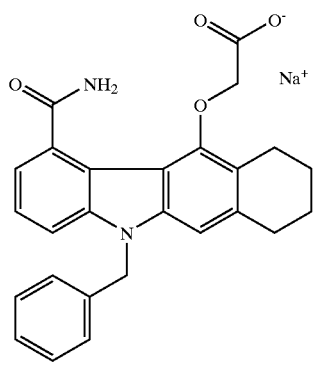

(C4)

(C5)

(C6)

(C7)

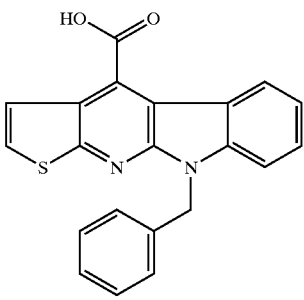

(C8)

The salts of the tetracyclic compounds represented by formulae (I), (II), (III), (IV), (V), (VI), (VII), and (VIII) are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of formula (I) (in a medium such as dimethylformamide) with 4-(2-chloroethyl)morpholine hydrochloride (available from Aldrich Chemical Co., Milwaukee, Wis. USA, Item No. C4, 220-3).

(III) Method of Preparing the Tetracyclic-5-amide Compound:

The tetracyclic-5-amide compounds are compounds of this invention and are also useful as intermediates or starting materials for preparing other compounds of the invention. The tetracyclic- 5-amide compounds are prepared by following a Scheme such as Scheme 1, as shown below:

Scheme 1

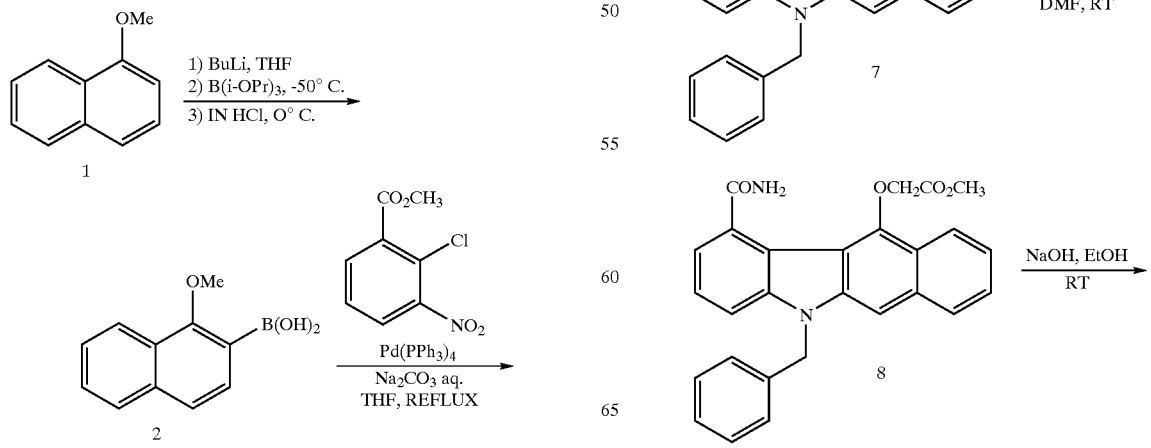

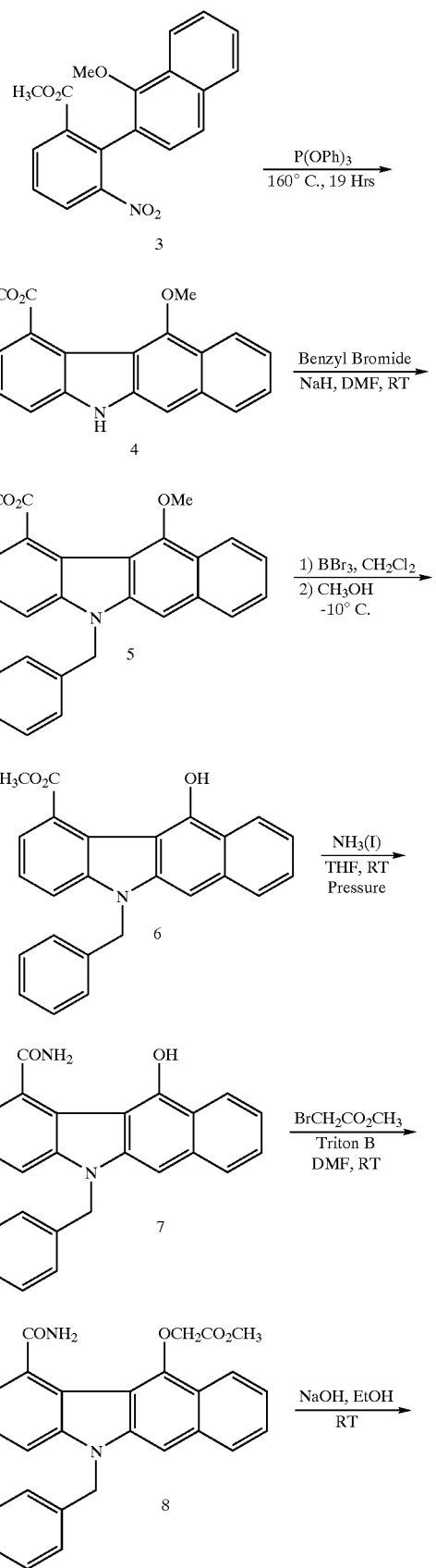

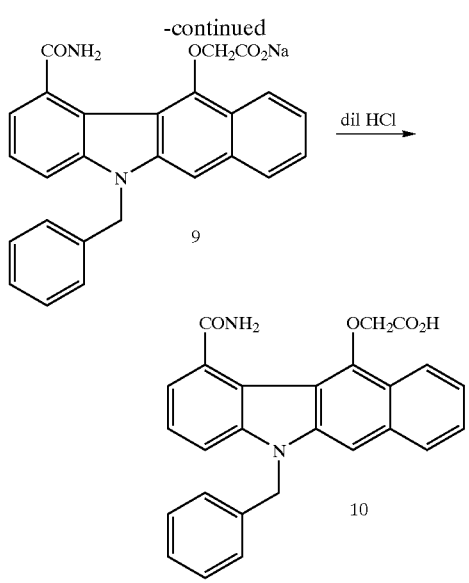

Scheme 1 depicts a protocol for preparing compounds of the invention wherein the D ring is a benzene ring system. By use of 1-methoxynaphthalene (available from Aldrich Chemical Co., Milwaukee, USA) substituted or unsubstituted at the 3 through 8 position(s), substituted analogs of compounds of the invention as disclosed, may be prepared. As shown, the reaction of 1-methoxynaphthalene with n-butyl lithium or similar organolithium reagent affords 2-lithio-1-methoxy naphthalene intermediate. Addition of a borate ester e.g., triisopropyl borate to the 2-lithio-1-methoxy naphthalene intermediate, generates the corresponding boronic acid compound (2) upon acidic work-up with, for example, aqueous HCl. The boronic acid compound (2) is then coupled with methyl-2-halo-3-nitrobenzoate (preferably chloro analog i.e., methyl-2-chloro-3-nitrobenzoate) in a Suzuki type coupling reaction (*Synth. Commun.*, 11, 513 (1981)). The reaction involves use of tetrakis(triphenylphosphine)palladium(0) or other suitable palladium catalyst, and a base such as sodium carbonate. Upon work-up and isolation, i.e., by chromatography, the coupling reaction product (3) is obtained. One of skill in the art is aware that substituted analogs of the compound (3) may be prepared by using methyl-3-halo-3-nitro benzoate reagents with non-interfering substituents at the 4, 5 and/or 6 position(s) of the benzene ring. The compound (3) is reductively cyclized to the carbazole-type tetracyclic compound of (4) using about a molar equivalent triphenyl phosphite under sealed tube conditions (see "The Reactivity of Organophosphorus Compounds. Part XIX. Reduction of Nitro-compounds by Triethyl Phosphite: A Convenient New Route to Carbazoles, Indoles, Indazoles, Triazoles, and Related Compounds," J. I. G. Cadogan, M. Cameron-Wood, R. K. Mackie, and R. J. G. Searle, *J. Chem. Soc.*, 1965, 4831.). The reductive cyclization reaction for converting compound (3) to compound (4) is performed at temperatures of about 100° C. to 180° C., preferably about 160° C. The compound (4) is alkylated or arylated at the carbazole nitrogen to introduce the $R_1$ group, by a base catalyzed deprotonation followed by a nucleophilic attack on an electrophile. Electrophiles suitable for this reaction are those necessary to incorporate the $R_1$ group described previously and include for example, alkyl, aryl, and arylalkyl groups as the halides, sulfonates or other leaving groups. For example the reaction of compound (4) with sodium hydride or a suitable base (i.e. n-BuLi, lithium triisopropyl amide, etc) in a suitable solvent e.g., dimethylformamide, followed by addition of benzyl bromide for example, affords upon work-up the compound of formula (5). The compound (5) is demethylated by reaction with boron tribromide or sodium thioethoxide in a suitable solvent such as dichloromethane. About 1.0 to 2.0 equivalents of boron tribromide is typically sufficient to effect complete de-methylation. The de-methylation reaction temperature is from about −12° C. to about 10° C. Work-up is effected by stirring with methyl alcohol, or other suitable protic solvent. The stirring in methyl alcohol is followed by neutralization with a base e.g. sodium bicarbonate. This is followed by extraction, and purification of the organic phase by methods known to one of skill; in the art, to afford compound (6).

A solution of compound (6) or analog thereof, in THF, is reacted with condensed ammonia in a sealed tube from a temperature of about 20° C. to about 70° C., preferably at about 50° C., over a period of 1 to 7 days, preferably 4 days. Condensed ammonia is obtained by running a stream of ammonia gas over the solution at about −78° C. as desired. Alternatively, the reaction can be performed by directly heating a mixture of excess ammonia gas and compound (6) in a sealed tube under temperature and time conditions as described above, to afford the compound (7).

The compound (7) is then subjected to a phase transfer coupling reaction with 2-bromomethylacetate using 2 non-interfering basic catalyst such as benzyltrimethylammonium hydroxide (triton-B, Rohm and Haas Corporation trademark) cesium carbonate, potassium carbonate, and the like, to afford the compound (8) or analog thereof based on starting material.

The compound of formula (8), itself, a compound of the invention, may be converted to the free acid or acid salt. The salt compound (9) or analog thereof, is obtained by reaction with sodium hydroxide (saponification) or lithium hydroxide in a suitable solvent e.g., THF. The product is isolated by drying or extraction into the aqueous phase followed by drying to afford compound (9) or analog thereof.

The free acid (10) is optionally obtained by acidifying the product of saponification (9) or other basification reaction, e.g. with lithium hydroxide. Most strong inorganic acids are suitable for acidification as described previously. However, the use of dilute HCl is preferred. The free acid (10) may be extracted into an organic phase if soluble, and dried by common laboratory methods or dried by removing water from the aqueous phase.

Compounds of formula I or intermediates thereto, wherein the D ring is a cyclohexyl or a substituted cylcohexane ring are prepared by starting with 6-methoxy-5-halo-1,2,3,8 tetrahydronaphthalene or analog substituted with non-interfering groups. The protocol according to Scheme 2 below;

Scheme 2

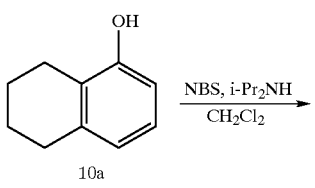

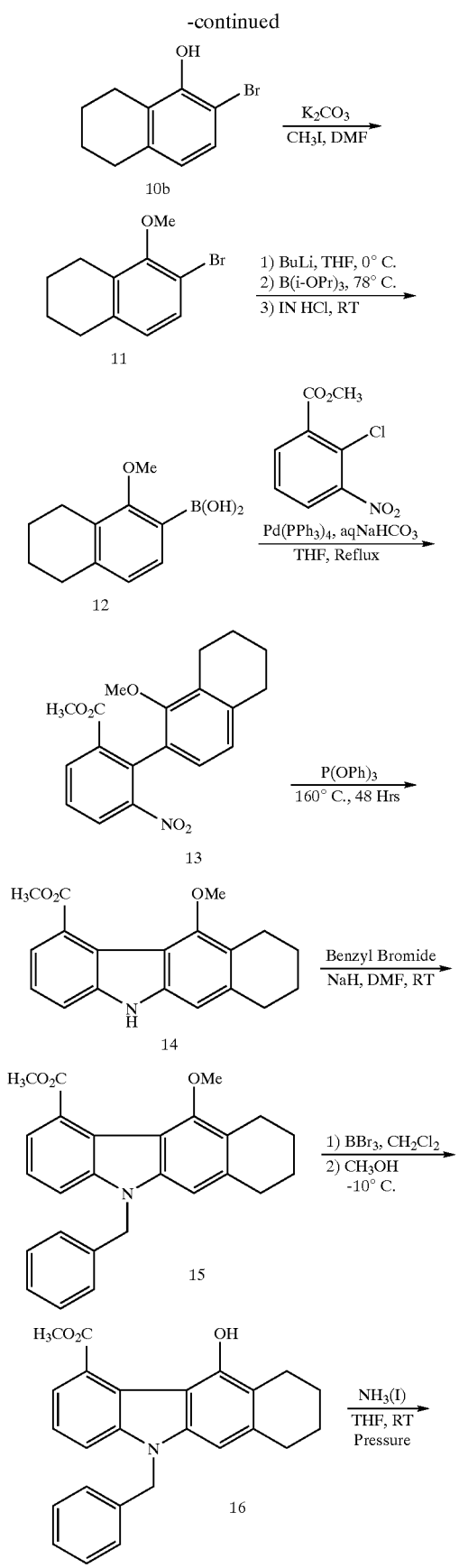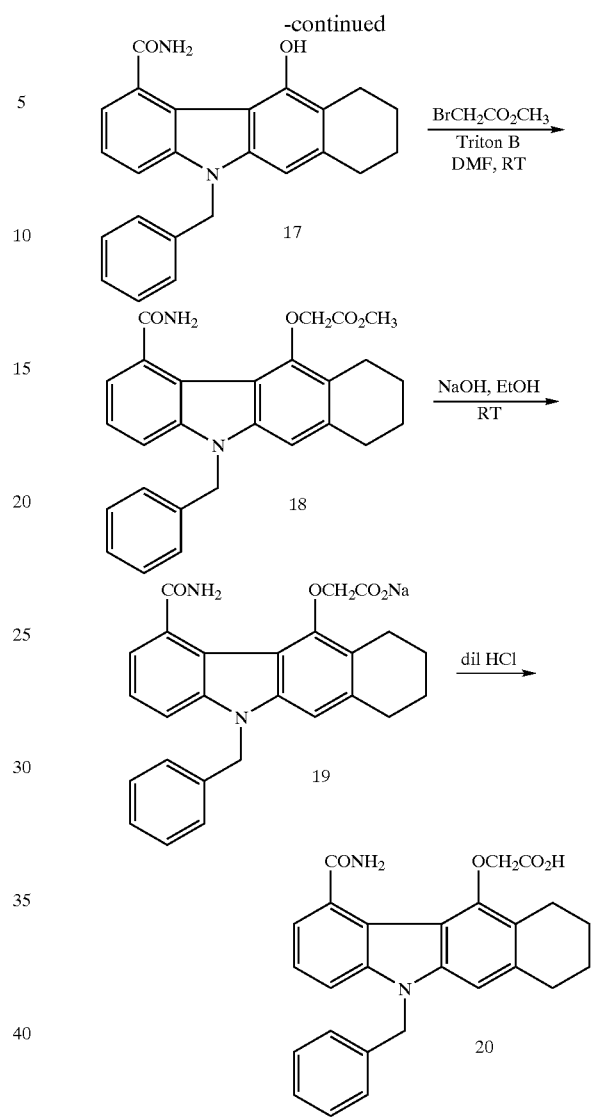

is exemplary for this class of compounds. The starting material 6-methoxy-5-halo-1,2,3,8 tetrahydronaphthalene (11) or analog thereof, is itself prepared from 5,6,7,8-tetrahydronaphthalene (10a) by a halogenation reaction using for example, n-bromosuccinimide to afford the 6-halo compound of formula (10b) or analog thereof. The compound (10b) is then methylated at the hydroxy group to afford the methoxy compound (11). The protocol of Scheme (2) is similar to that of Scheme (1) except for the starting material. The compound (18) is saponified to the sodium salt (19) or converted to other salts and/or hydrolyzed to the free acid (20).

Similarly, compounds of formula I wherein the C and D rings together constitute a naphthyl group, are obtained from the compound (18) prepared as shown in Scheme 2, by aromatization of the D ring with for example, DDQ (2,3-dichloro-5,6-dicyanobenzoquinone—Lancaster Synthesis, Aldrich Chemical Co.). For example, aromatization of compound (18) affords compound (8) of Scheme 1. Compound (8) of scheme 1 can be elaborated to the sodium salt and or acid as shown in Scheme 1. The aromatization reaction to convert compound (18) to compound (8) is performed in a suitable solvent such as 1,4-dioxane at about reflux (about the boiling point of 1,4-dioxane) temperatures for about 1 to 3 hours, preferably 1 hour. A protocol according to Scheme (3)
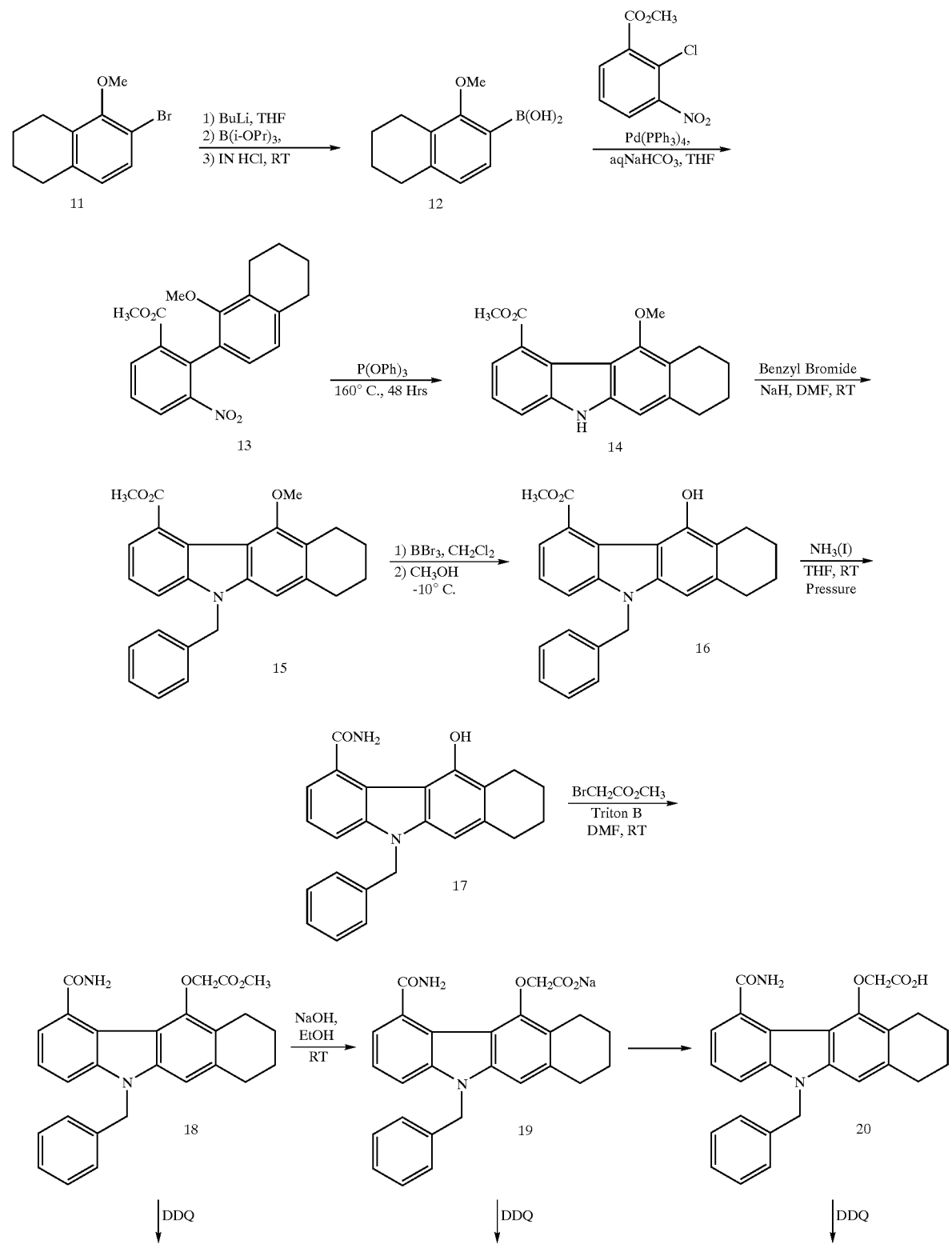
Scheme 3

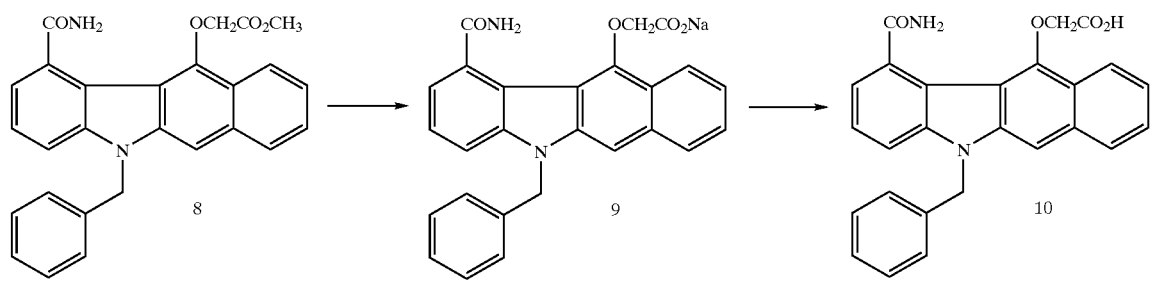

represent the steps to the naphthyl compounds (C+D ring=naphthyl) discussed above. The aromatization reaction results in an isolable intermediate methyl ester compound (a compound of the invention), which is optionally saponified to the intermediate sodium salt and/or hydrolyzed to the free acid compound (20).

Methods for preparing the hydrazide (hydrazone) compounds of the invention include the method represented below in scheme 4:

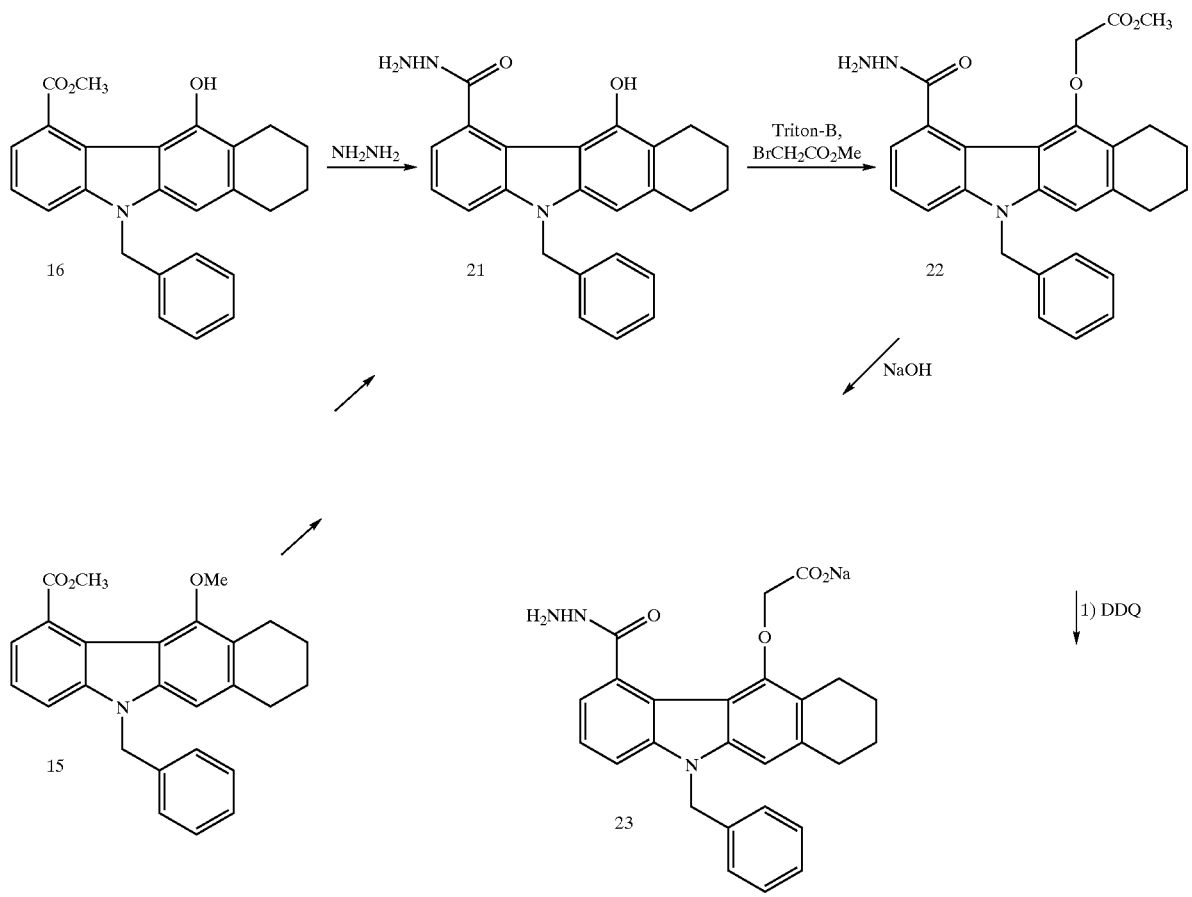

-continued

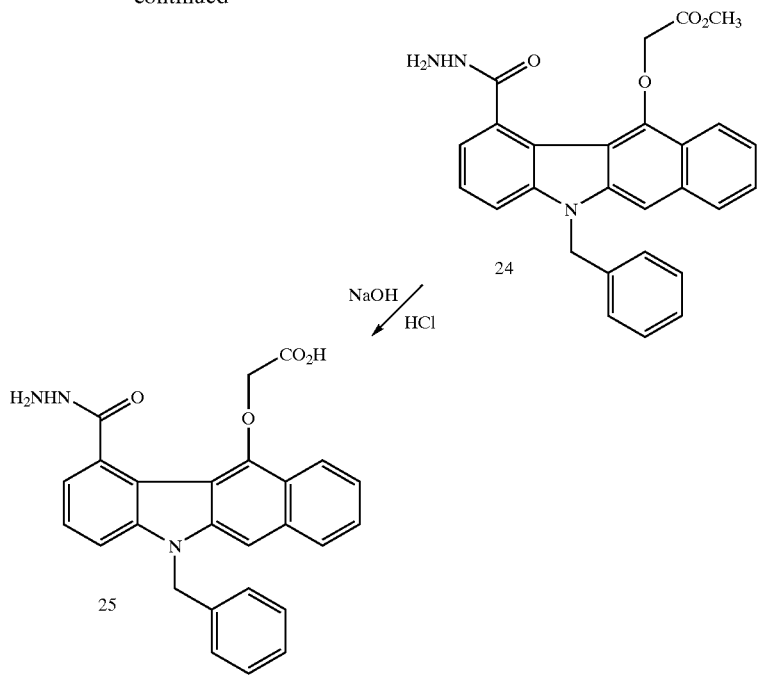

According to scheme 4, the compound (16) obtained as described above (scheme 3) may be converted to a hydrazide (hydrazone) compound of the invention, e.g. compound (21), by reaction with hydrazine. Alternatively compound (15) may be reacted with hydrazine to afford an intermediate hydrazone compound which may be further dealkylated at the (6) position using boron tribromide or sodium thioethoxide as described previously, to form the hydroxy compound (21). The dealkylated compound (21) is reacted with bromomethyl acetate under basic catalysis conditions using for example, triton-B™ as described above, to afford the ester (22). The ester (22) may be hydrolyzed to afford the corresponding acid compound, saponified to the sodium salt, or aromatized to the compound of formula (24). Optionally, the aromatized compound (24) may be converted to the acid (25) by use of a base such as sodium hydroxide or lithium hydroxide in a suitable solvent or solvent-mixture followed by acidification (i.e., acid wash).

The Tetracyclic-6-glyoxylamide Compounds or Intermediates

The tetracyclic glyoxylamide intermediates and compounds of the invention may be prepared by reacting 1,2 dichloro-3-nitrobenzene with the compound (12) in place of 1-chloro-2-methoxy-3-nitrobenzene as shown in Scheme 5 below:

Scheme 5

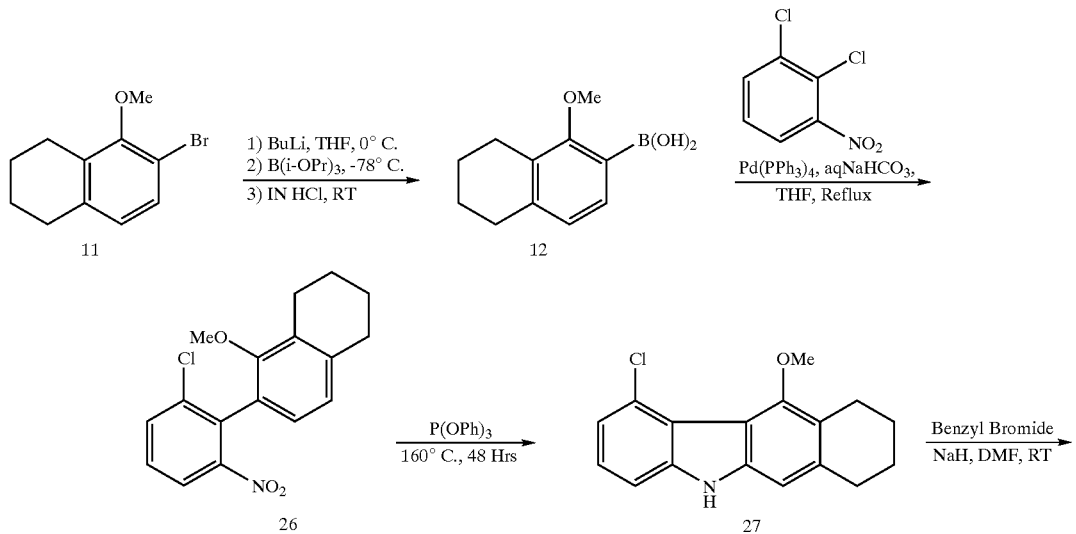

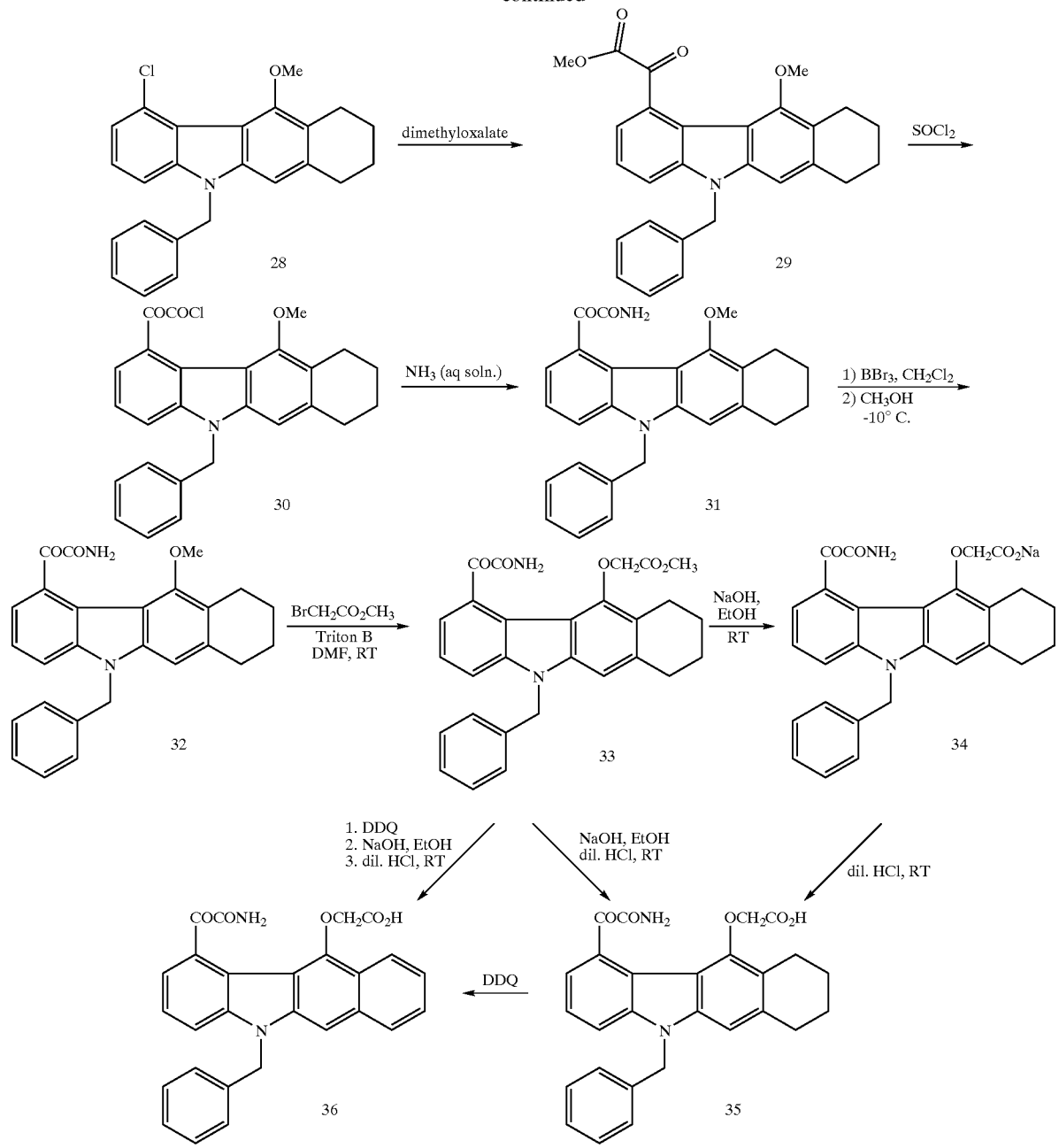

Alternatively, 1-chloro-2-bromo-3-nitrobenzene may be reacted with the compound (12). Compound (12) is prepared as described previously in Scheme (2). In either case a mixture of products is possible and the desired product (26) is isolated and purified by chromatography, distillation, crystallization or a combination of these methods. Again, the Suzuki type coupling is employed to afford the compound (26). The compound (26) is reacted with triphenylphosphite as in Scheme (1) or (2) to afford the reductive cyclization product (27). The compound (27) is alkylated at the carbazole nitrogen atom by reaction with a molar or slight excess, of NaH in a polar aprotic solvent, such as for example dimethylformamide, followed by addition of an electrophile such as for example, benzylbromide, to afford the compound (28). The compound (28) is reacted with n-butyl lithium or other suitable base to afford by a metal-halogen exchange reaction, an un-isolated lithio-intermediate for example. This is followed by addition of dimethyl oxalate to the lithio-intermediate to afford the methyl oxalate compound (29). Reaction of compound (29) with a halogenating agent i.e. anhydrous HCl, thionyl chloride, affords the halogen compound (e.g. chloride (30)). The compound (30) or analog thereof, is reacted with ammonia condensate (condensation of ammonia gas by cooling to form liquid ammonia as discussed previously) to afford the glyoxylamide compound (31). The ammonation may be accomplished by reacting compound (30) and ammonia in a pressure vessel at about 30 to 80° C. for about 10 minutes to 4 hours, followed by appropriate cooling (i.e. about −78° C.), and isolation of product. Compound (31) is then demethylated at the 6 position (or at the 7 position if starting with a compound that places methoxy group at the 7 position). De-methylation is accomplished by reaction with boron tribromide following a procedure described in the examples to afford the compound (32) having a hydroxyl group at position 6 (or 7 as the case may be). The compound (32) may be elaborated to the oxyacetic acid methyl ester derivative (33) by reaction with bromoacetic acid methyl ester (methylbromoacetate) to afford the methyl ester (33). Formation of compound (33) is accomplished in the presence of a phase transfer catalyst such as tetra-n-butylammonium bromide, or triton-B™. The methyl ester (33) may be saponified to the salt i.e. sodium salt (34) using sodium hydroxide or to the potassium salt using potassium hydroxide optionally, the salt, i.e. sodium salt (34) may be hydrolyzed to the acid (35) using dilute HCl or other suitable acids. The acid (35) may be aromatized to the naphthyl compound (36). Alternatively, the methylester (33) may be aromatized to an intermediate naphthyl compound followed by saponification and acidification (i.e. sodium hydroxide treatment followed by acid wash) to the acid (36)

The Tetracyclic-5-acetamide Compounds

The tetracyclic compounds of the present invention having the acetamide group at position (5) may be prepared as shown in Scheme 6 below.

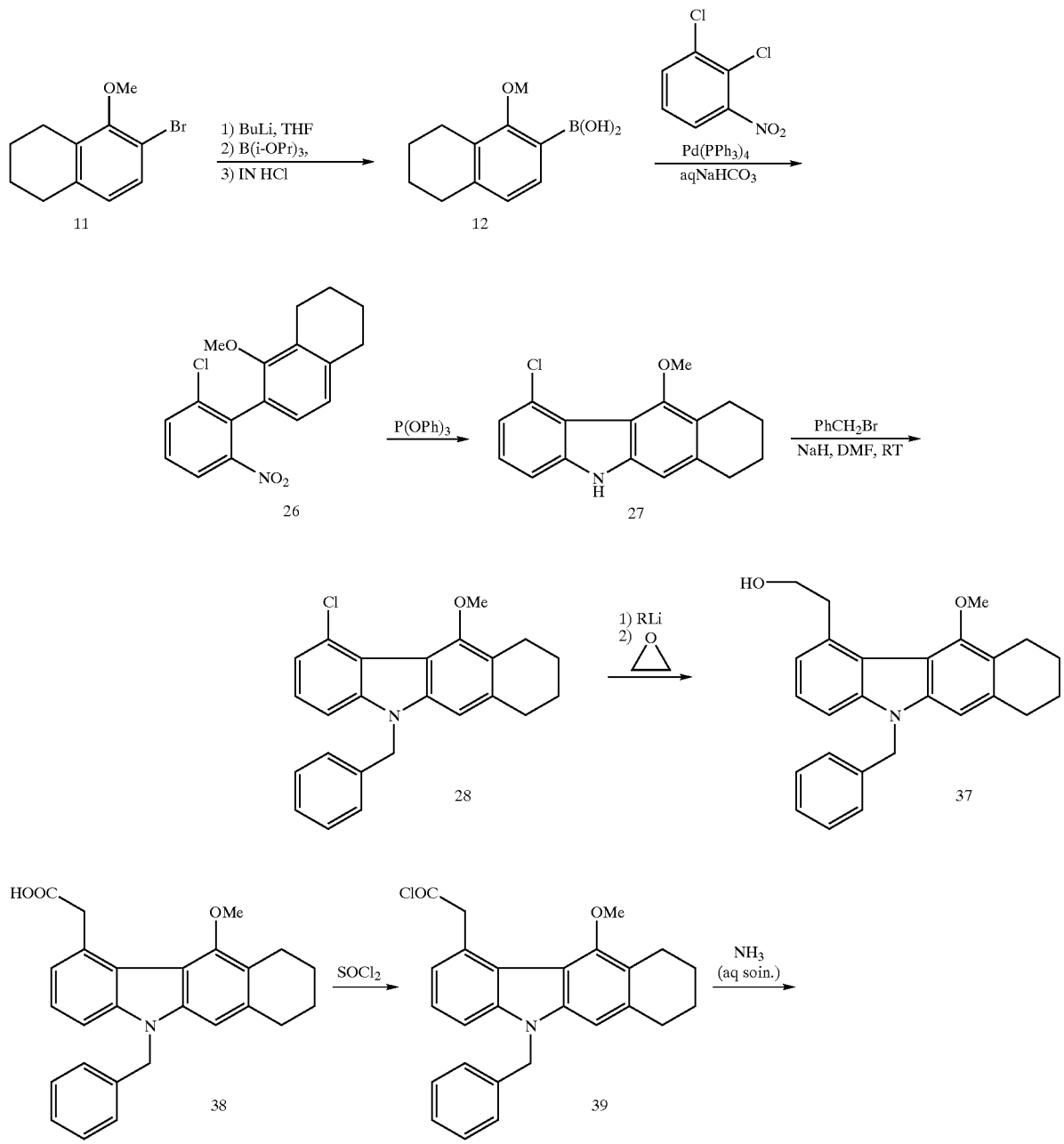

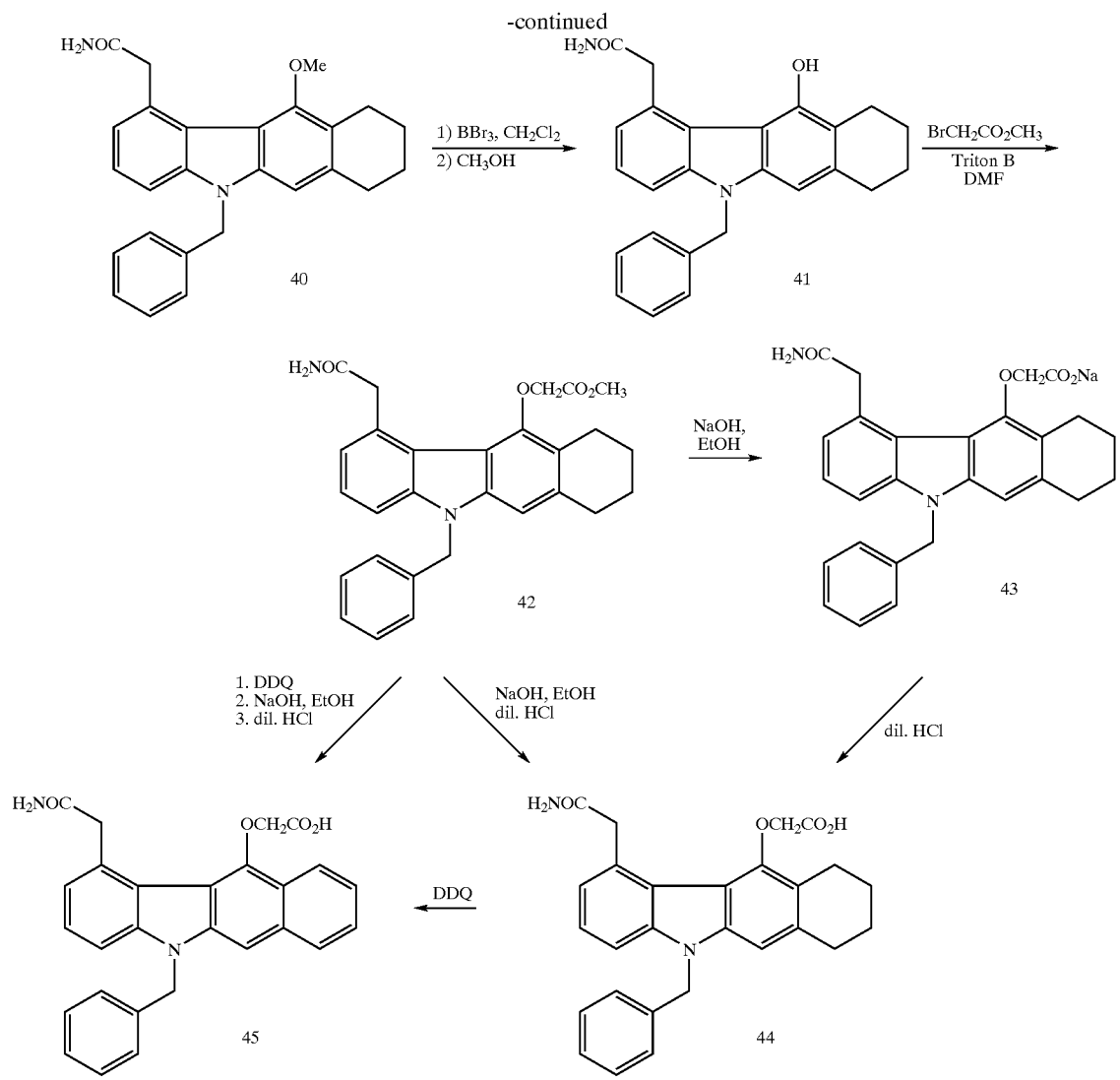

Starting with compound 11, the compounds 26, 27 and 28 are prepared as discussed above according to scheme 5. The compound (28) is subjected to a metal-halogen exchange reaction by the use of n-butyl lithium, t-butyl lithium, or other suitable organic base to afford a lithio intermediate (for example) under inert conditions and polar aprotic solvent(s). To the above lithio-intermediate compound is added a terminal epoxide, (i.e. ethylene oxide), to afford the terminal alcohol (37) by a nucleophilic ring opening reaction upon aqueous acidic work-up. The terminal alcohol product (37) is isolated preferably by aqueous work up or by other methods known to one of skill in the art. The terminal alcohol (37) is oxidized to the acid (38), for example by use of sodium hypochlorite or other terminal alcohol oxidizing agents. Other oxidizing agents for the conversion of terminal primary alcohol to the acid are known to one of skill in the art. The acid (38) is converted to an acid chloride (39) by reaction with, for example thionyl chloride, which is then ammoniated to afford the acetamide (40). Alternatively, the acid (38) is converted to the amide i.e. acetamide (40) by reaction with ammonia as described supra or by use of amide forming reagents and conditions known to one of skill in the art or taught in reference literature such as for example, J. March, *Advanced Organic Chemistry*, 3$^{rd}$ edition, John Wiley Publishing NY, N.Y.

Other methods may include use of reagents for conversion of acids to amides such as the use of activated ester intermediates such as that obtained by use of DCC, DCU, or benzotriazole reagents (R. C. Larock, *Comprehensive Organic Transformations* 2$^{nd}$ edition, Wiley-VCH, NY, N.Y., 1941, (1999)). The acetamide (40) is then demethylated with boron tribromide as described supra to afford the hydroxy compound (41). This is followed by elaboration of the hydroxy group of compound (41) to the oxymethyl acetate derivative (42). This is accomplished for example, by a basic catalysis reaction with methyl bromoacetate and cesium carbonate or TRITON-B™ in methylene chloride. The methylester compound (42) may be saponified to the sodium salt (43) followed by hydrolysis to the acid (44) following a procedure described previously. The acid (44) may be aromatized to the naphthyl compound (45).

Alternatively, the methyl ester (42) may be aromatized and hydrolyzed to the acid (45) by a procedure described previously in scheme 5.

49

Preparing the Tetracyclic-5-oxime Compounds:
The tetracyclic-5-oxime compounds of the invention can be prepared following the protocol of scheme 7 below;

50 other metal salt (not shown) depending on the base used; or (b) aromatized to the naphthyl compound (47) by using DDQ under reaction conditions similar to that described in

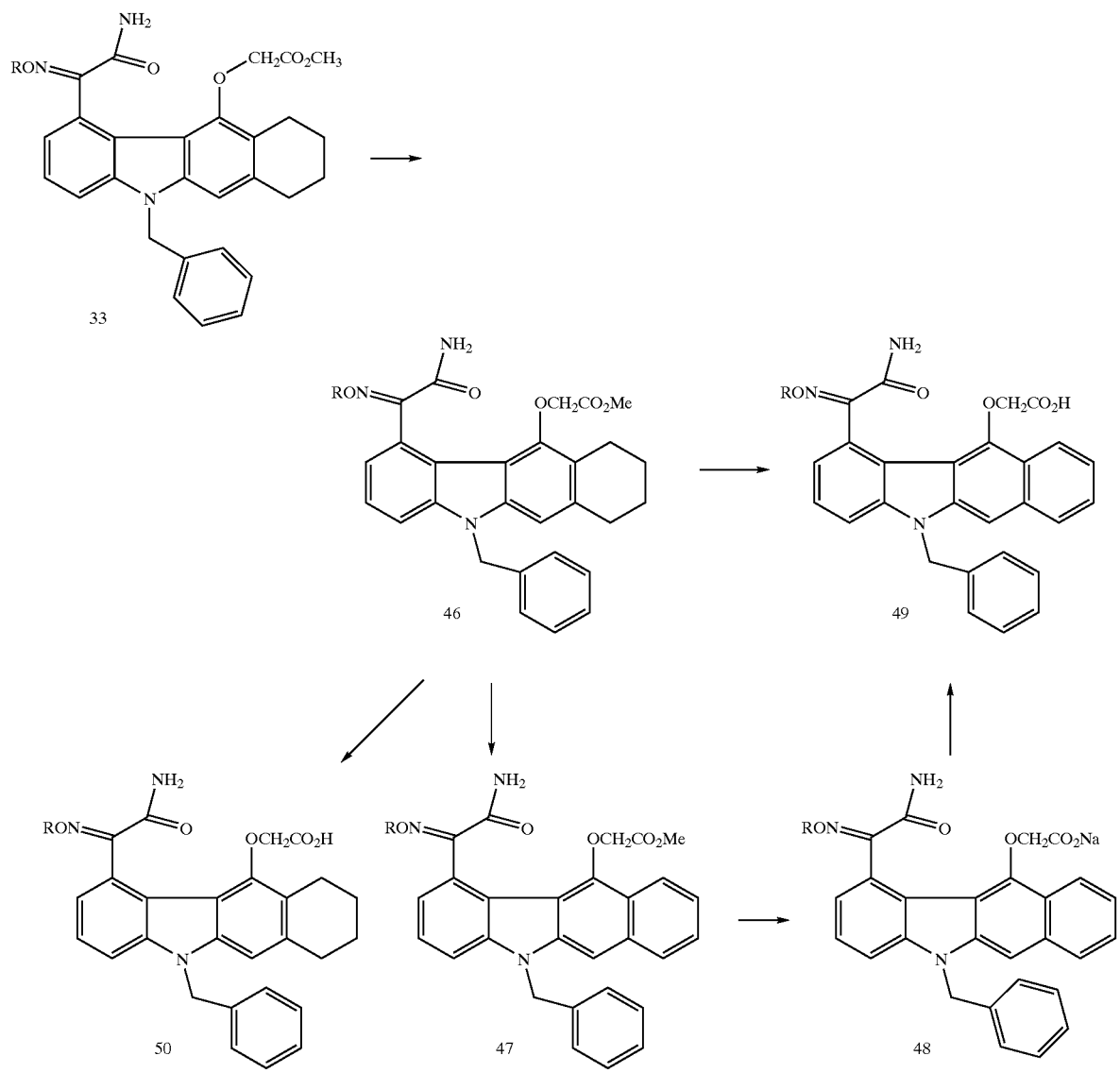

To introduce the oxime functionality, the methyl ester of the tetracyclic glyoxylamide (compound 33 in scheme 5) is heated with hydroxylamine hydrochloride (when R is H) in a THF/methanol mixture for about 1 to 8 hours or until the reaction is deemed complete. The reaction product is isolated by chromatography or other known laboratory procedure. Substituted oximes such as when R is methyl, ethyl, phenyl or other substituent can be prepared by reacting the corresponding substituted hydroxylamine hydrochloride or free base with the glyoxylamide (33) as described supra. The ester functionality at the 6 or 7 position on the resulting tetracyclic nucleus, as in for example, compound (46) can be: (a) converted to the acid by hydrolysis using lithium hydroxide or other known ester hydrolysis methods to afford compound (50); via the sodium salt, or potassium salt, or the examples. The compound of formula (47) may than be hydrolyzed to the free acid compound (49) via the sodium salt (48). Compound (46) could be aromatized and then hydrolyzed to afford compound (49) directly.

The Acylamino acid Compounds

The acylamino derivatives of compounds 9, 19, 20, 23, 25, 35, 36, 43, 44, 48 or 49 representing compounds described above as per schemes 1 through scheme 7. Any of the compounds 9, 19, 20, 23, 25, 35, 36, 43, 44, 48 or 49 each having a oxyacetic acid group at the 6 position may be converted to the corresponding acylamino acid compound by reaction with a C-terminal protected amino acid. Where a C-terminal protected amino acid is used, the protected amide compound or the resulting oxo-amino acid compound (e.g. compound 51 infra) is also a compound of the present invention. For example, the tetracyclic-5-glyoxylamide-6-acylamino acid derivative compounds of the invention are prepared by room temperature base catalyzed condensation of the amino acid protected at the C-terminus by a protecting group known in the literature (preferably as the methyl ester), with the tetracyclic-5-glyoxylamide acid derivative compound of formula (35), for example, as shown in Scheme 8 below:

The product of the condensation reaction (51) itself a compound of the invention is hydrolyzed to the free acid, i.e., to remove the amino acid protecting group. Typically, the condensation or coupling is performed in a solvent such as dimethylformamide, tetrahydrofuran or aqueous mixtures of the like. In general protic solvents are preferred for the purpose of this invention. The reaction is base catalyzed, including use of weak organic or inorganic bases. Organic bases such as collidine are preferred. The reaction is also

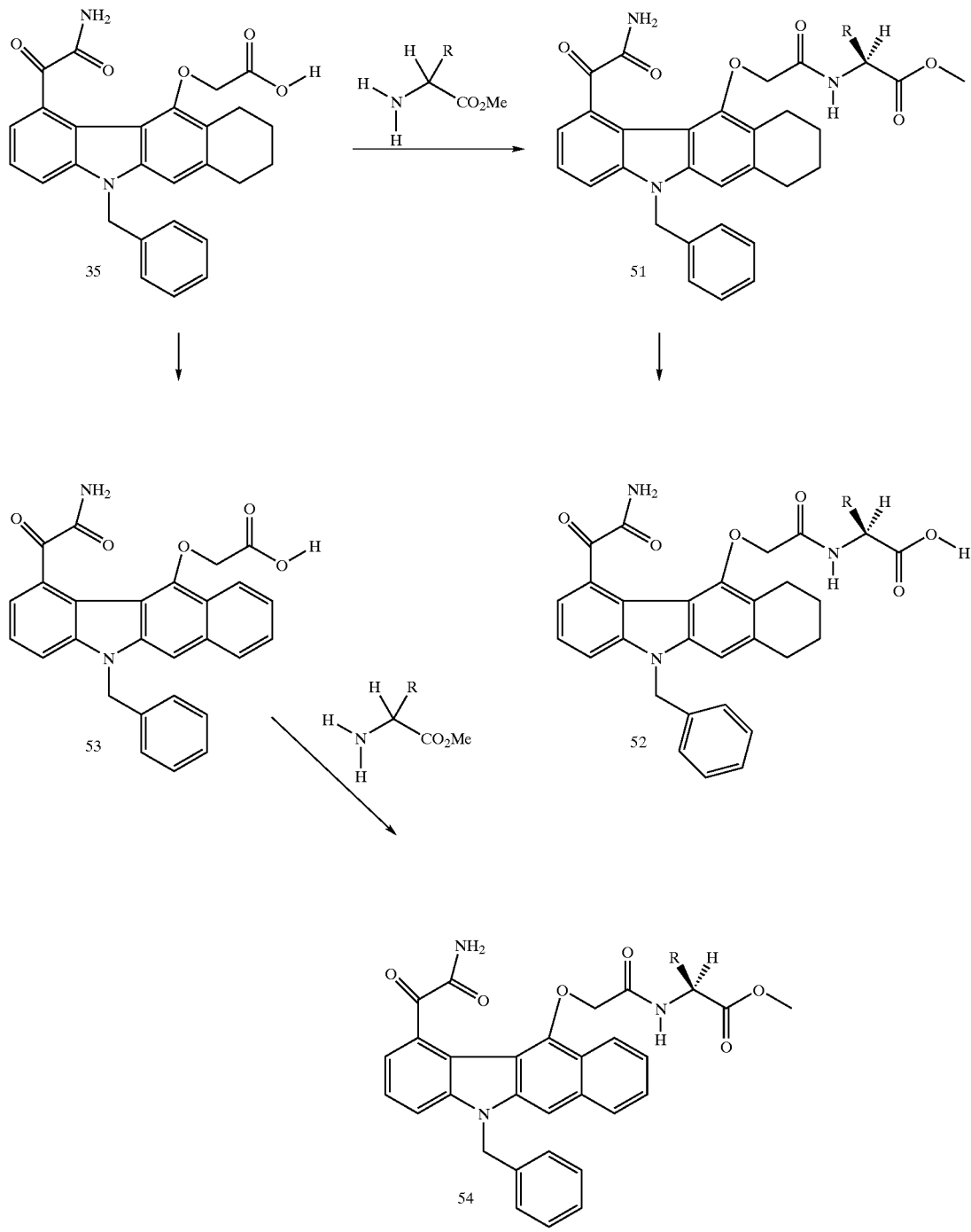

Scheme 8 preferably run in the presence of agents that retard or reduce racemization of the amino acid or its derivative, such as for example, benzotriazolyl-N-oxy-tris(dimethylamino)phosphonium hexafluorophosphate. Upon completion of the reaction, the mixture is concentrated in vacuo. The resulting product mixture is chromatographed or subjected to crystallization conditions to obtain the target compound (i.e. compound (52)).

The compound (35) could alternatively be aromatized utilizing DDQ as described previously, to afford the compound (53). The compound (53) is then coupled with a protected acylamino acid group as shown to afford the corresponding acylamino acid derivative (54) where the C and D rings are fused to form a naphthalenyl ring system.

Other suitable amino acid forming reactions and methods are applicable to introduce the acylamino acid functionality and are well known in the art. References texts include for example J. March *Advanced Organic Chemistry*, Wiley Interscience publishers, New York, N.Y, 1985, and R. C. Larock *Comprehensive Organic Transformations*, VCH Publishers, New York, N.Y., 1989.

Acylamino acid derivatives of the tetracyclic oximes, oxime amide, thioacetamides and acetamides may be prepared from the corresponding acid such as compound (49) (Scheme 7) by methods described above for preparing the acylamino acid derivatives of the glyoxylamide compounds. For example the oxime amide compound (49) (Scheme 7), above may be converted to the corresponding acylamino acid derivative by an amide coupling reaction. Similarly, the tetracyclic-5-acetamide oxyacid compounds (i.e. compound (44)), may be converted to the corresponding acylamino acid derivative at the 6 or 7 position as described previously.

Preparing the Tetracyclic-6-N-hydroxyfunctional Amide Compounds

The tetracyclic-5-glyoxylamide-6-N-hydroxyfunctional amide compounds of the invention may be prepared from the compounds 10, 20, 23, 25, 35, 36, 43, 44, 48 or 49 representing the tetracyclic-5-amide, the tetracyclic-5-hydrazide, the tetracyclic-5-glyoxylamide, the tetracyclic-5-acetamide and the tetracyclic-5-oxime compounds prepared as described previously. Any of the compounds 10, 20, 25, 31, 38 or 40 each having a oxyacid group at the (6) position may be converted to the corresponding N-hydroxyfunctional amide compounds of the present invention by methods known to one of skill in the art. In the protocol beginning with acid compound (10), the acid (10) is converted to the N-hydroxyfunctional amide compound (55) as shown in Scheme 9 below:

Scheme 9

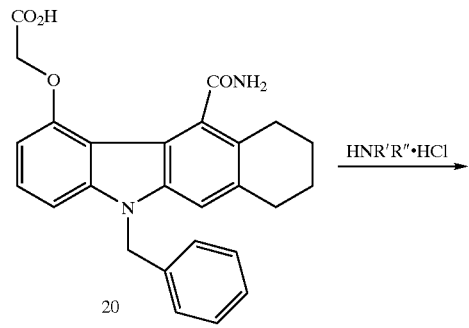

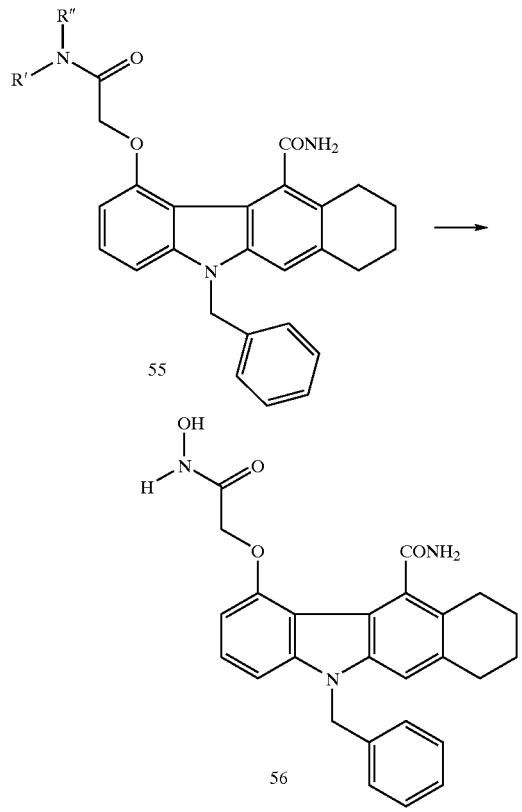

The above transformation may be accomplished by coupling the compound of formula (20), prepared from compound (18) as shown in Scheme 2, with a protected and/or substituted or unsubstituted hydroxylamine group or derivative, in the presence of a coupling agent. This results in a protected N-hydroxyfunctional amide derivative compound (55). For example, the acid compound (20) is reacted with o-(tert-butyldimethylsilyl) hydroxylamine at ambient temperature, in the presence of excess 2,4,6-collidine (collidine) and benzotriazol-1-yl -oxytris(dimethylamino)phosphonium hexafluorophosphonate (coupling catalyst, see *Tetrahedron Lett.*, 1219 (1975)) to afford after about 1–10 hours, the o-(tert-butyldimethylsilyl) substituted N-hydroxyfunctional amide derivative (55). The silyl or other protecting group is removed by well known methods such as for example, the use of trifluoroacetic acid for removal of silyl protecting groups) to afford, for example, the N-hydroxyfunctional amide compound (56) wherein $R^{6a}$ is hydroxy and $R^{6b}$ is hydrogen.

Typically, the condensation or coupling is performed in a solvent such a dimethylformamide, tetrahydrofuran or aqueous mixtures of the like. In general protic solvents are preferred for the purpose of this invention. A base including for example, weak organic or inorganic bases catalyzes the reaction. Organic bases such as collidine are preferred. The reaction is also preferably run in the presence of agents that retard or reduce racemization of the hydroxyfunctional amide, the substituted hydroxylamine or its derivative. A particularly preferred agent is benzotriazolyl-N-oxy-tris(dimethylamino)phosphonium hexafluorophosphate. Upon completion of the reaction, the mixture is concentrated in vacuo. The resulting product mixture is chromatographed or crystallized, e.g., by sonication to obtain the target compound.

An alternate preparation method is the inter-conversion of compounds of the invention as shown for example in Scheme (10):

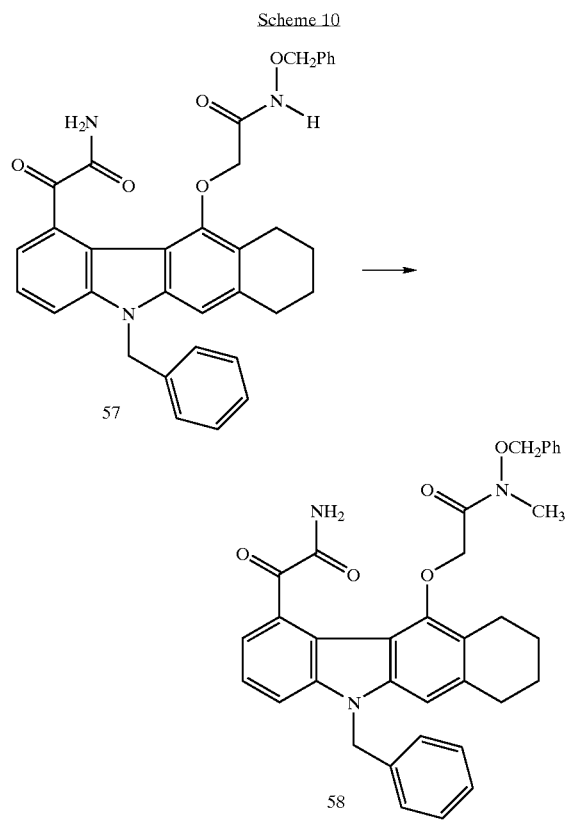

The conversion of a compound of formula (57) to a compound of formula (58) may be accomplished, for example, by base catalyzed alkylation with n-BuLi and methyl iodide. These and other methods of functional group inter-conversions and are well known in the art and can be found in reference texts such as for example J. March *Advanced Organic Chemistry*, Wiley Interscience publishers, New York, N.Y., 1985, and R. C. Larock *Comprehensive Organic Transformations*, Wiley-VCH Publishers, New York, N.Y., 1999.

Other tetracyclic-6-hydroxyfunctional sPLA$_2$ derivative compounds disclosed herein, including for example, the tetracyclic-5-acetamide-6-hydroxyfunctional amide derivative sPLA$_2$ inhibitors. These are similarly prepared by condensation of a protected or unprotected, substituted or unsubstituted hydroxylamine or derivative thereof, as discussed above.

IV. Methods of Using the Compounds of the Invention:

The tetracyclic compounds described herein are believed to achieve their beneficial therapeutic action principally by direct inhibition of mammalian (including human) SPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with a therapeutically effective amount of tetracyclic compounds corresponding to Formulae (I) or (II) or (III) or (IV) or (V) or (VI) or (VII) or (VIII) as described herein including a combination thereof, a salt or a prodrug derivative thereof.

Another aspect of this invention relates to a method for treating Inflammatory Diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of a tetracyclic compound of the invention.

As previously noted the compounds of this invention are useful for inhibiting SPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effect will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention per Formula (I) or (II) or (III) or (IV) or (V) or (VI) or (VII) or (VIII) or pharmaceutical formulations containing these compounds are in unit dosage form for administration to a mammal. The unit dosage form can be a capsule or tablet itself, or the appropriate number of any of these. The quantity of Active Ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the tetracyclic compound of the invention together with a pharmaceutically acceptable carrier or diluent therefor. The present pharmaceutical formulations are prepared by known procedures using well-known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or (II) or (III) or (IV) or (V) or (VI) or (VII) or (VIII) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| | |
|---|---|
| Active ingredient | 225 mg |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A. Dennis, *Analytical Biochemistry*, 204, pp. 190–197, 1992 (the disclosure of which is incorporated herein by reference):

Reagents:
   REACTION BUFFER—
      $CaCl_2.2H_2O$ (1.47 g/L)
      KCl (7.455 g/L)
      Bovine Serum Albumin (fatty acid free) (1 g/L)
         (Sigma A-7030, product of Sigma Chemical Co., St. Louis Mo., USA)
      TRIS HCl (3.94 g/L)
      pH 7.5 (adjust with NaOH)
   ENZYME BUFFER—
      0.05 $NaOAc.3H_2O$, pH 4.5
      0.2 NaCl
      Adjust pH to 4.5 with acetic acid
   DTNB—5,5'-dithiobis-2-nitrobenzoic acid
   RACEMIC DIHEPTANOYL THIO—PC racemic 1,2-bis(heptanoylthio)-1,2-dideoxy-sn-glycero-3-phosphorylcholine
      TRITON X-100™ prepare at 6.249 mg/ml in reaction buffer to equal 10 uM.
   REACTION MIXTURE—

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;

2. Add 10 ul test compound (or solvent blank) to appropriate wells, mix 20 seconds;

3. Add 50 nanograms of $sPLA_2$ (10 microliters) to appropriate wells;

4. Incubate plate at 40° C. for 30 minutes;

5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

Results

| Compound of Example# | $IC_{50}$ (uM) (micromolar) |
| --- | --- |
| 1 | 38.6 |
| 2 | 410 |

While the present invention has been illustrated above by certain specific embodiments, it is not intended that these specific examples should limit the scope of the invention as described in the appended claims.

Experimental

All of the products of the Examples described below as well as intermediates used in the following procedures showed satisfactory NMR and IR spectra. They also had the correct mass spectral values.

EXAMPLE 1

(5-Benzyl-1-carbamoyl-5H-benzo[b]carbazol-11-yloxy)-acetic acid, sodium salt

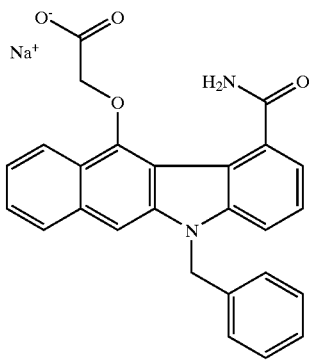

1. Preparation of 1-Methoxynaphthalene-2-boronic acid

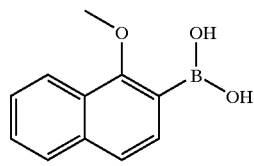

To a stirred mixture of 1-methoxynaphthalene (20.0 g, 126.6 mmol) in THF (100 mL) was added n-butyllithium (53.16 mL, 132.9 mmol, 2.5M solution in hexanes) at room temperature over 5 min. The reaction mixture was cooled to −50° C., and triisopropyl borate (43.8 mL, 35.7 g, 190 mmol) was added dropwise over 0.25 h. The resulting precipitate was broken up by the addition of THF (100 mL), and the mixture was allowed to warm to 0° C. with stirring. At this point the mixture was poured into 1N HCl (100 mL), the product extracted with ethyl acetate, the combined extracts dried over anhydrous sodium sulfate, and filtered. After concentrating the filtrate in vacuo at ambient temperature, the residue was partially dissolved in diethyl ether, triturated with hexane, and the resulting precipitate filtered and washed with hexane to afford 10.64 g (41%) of the title compound 1-methoxynaphthalene-2-boronic acid as an off-white crystalline solid (MW 202.02, $C_{11}H_{11}BO_3$).

$^1$H NMR (DMSO-$d_6$) δ 8.08–8.06 (m, 1H), 7.87–7.84 (m, 1H), 7.56 (d, 1H, J=8 Hz), 7.50–7.46 (m, 3H), 6.51 (br s, 2H), and 3.91 (s, 3H).

1a. Preparation of 2-Chloro-3-nitrobenzoic acid, methyl ester

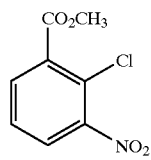

A solution of 2-chloro-3-nitrobenzoic acid (20.16 g, 100 mmol), iodomethane (15.6 g, 110 mmol), and potassium carbonate (15.0 g, 108.5 mmol) in DMF (100 mL) was stirred at room temperature for 48 h. The mixture was poured into 1.5 liters of $H_2O$. The resultant precipitate was collected by filtration, washed with $H_2O$, and dried in vacuo to afford 20.0 g (93%) of the title compound 2-chloro-3-nitrobenzoic acid, methyl ester as a white solid (MW 215.59).

$^1$H NMR (CDCl$_3$) δ 8.42 (dd, 1H, J=1 and 8 Hz), 8.18 (dd, 1H, J=1 and 8 Hz), 7.43 (t, 1H, J=8 Hz), and 3.9 (s, 3H). IR (KBr, cm$^{-1}$) 1743, 1719, 1595, 1540, 1532, 1433, 1357, 1300, and 730. MS (FD) m/e 215, 216. Anal. Calcd. for $C_8H_6NClO_4$: C, 44.57; H, 3.81; N, 6.50. Found C, 44.19; H, 3.45; N, 6.19.

2. Preparation of 2-(1-Methoxynaphthalen-2-yl)-3-nitrobenzoic acid, methyl ester

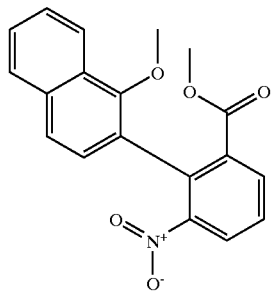

A solution of 2-chloro-3-nitrobenzoic acid methyl ester, (2.16 g, 10.0 mM), 1-methoxynaphthalene-2-boronic acid, (2.22 g, 11.0 mM), tetrakis(triphenylphosphine) palladium (0)(0.584 g, 0.5 mM), and 2M aqueous sodium carbonate solution (10.5 mL, 21.0 mM) in THF (50 mL) was stirred at reflux for 31 h in the absence of light. The mixture was cooled to room temperature, the THF removed in vacuo, and the resulting aqueous residue dissolved in ethyl acetate and brine. The solvent layers were separated, the aqueous layer extracted with ethyl acetate (4×25 mL), the combined ethyl acetate extracts washed successively with $H_2O$, 1N HCl, saturated aqueous $NaHCO_3$ solution, and saturated brine, dried over magnesium sulfate, filtered, and concentrated in vacuo. The resultant oil was purified by column chromatography on silica gel (elution with 1:1 chloroform/toluene) to afford 2.54 g (75%) of the title compound 2-(1-methoxynaphthalen-2-yl)-3-nitrobenzoic acid, methyl ester as a yellow solid (MP 139–141° C., MW 337.34).

$^1$H NMR (CDCl$_3$) δ 8.13–8.11 (m, 1H), 8.08 (d, 1H, J=9 Hz), 8.00 (d, 1H, J=9 Hz), 7.86–7.84 (m, 1H), 7.64 (d, 1H, J=9 Hz), 7.60 (d, 1H, J=8 Hz), 7.52–7.49 (m, 2H), 7.21 (d, 1H, J=8 Hz), 3.61 (s, 3H), and 3.53 (s, 3H). IR (KBr, cm$^{-1}$) 3020–2830 (multiple peak grouping), 1737, 1531, 1369, 1277, 1109, and 757. MS (ESI) m/e 306, 338, 360. Anal. Calcd for $C_{19}H_{15}NO_5$: C, 67.65; H, 4.48; N, 4.15. Found C, 65.77; H, 4.31; N, 4.00.

3. Preparation of 11-Methoxy-5H-benzo[b]carbazole-1-carboxylic acid, methyl ester

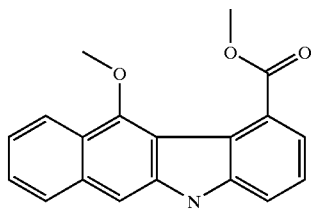

A solution of 2-(1-methoxynaphthalen-2-yl)-3-nitrobenzoic acid, methyl ester, (1.52 g, 4.5 mM) in triphenyl phosphite (7.19 g, 6.1 mL, 22.5 mM) was heated at 160° C. for 19 h under a nitrogen atmosphere. The mixture was cooled to room temperature and dried azeotropically in vacuo with toluene, then purified by column chromatography on silica gel (elution with gradient hexane/ethyl acetate) to afford 0.37 g (27%) of the title compound 11-methoxy-5H-benzo[b]carbazole-1-carboxylic acid, methyl ester as a yellow solid (MP 190–196° C., MW 305.34).

$^1$H NMR (CDCl$_3$) δ 8.27 (d, 1H, J=9 Hz), 8.08 (br s, 1H), 7.89 (d, 1H, J=9 Hz), 7.54 (s, 1H), 7.50–7.45 (m, 3H), 7.41 (d, 1H, J=7 Hz), 7.32 (d, 1H, J=8 Hz), 4.03 (s, 3H), and 3.91 (s, 3H). IR (CHCl$_3$, cm$^{-1}$) 3469, 3030–2850 (multiple peak grouping), 1725, 1641, 1606, 1433, 1400, 1343, 1303, 1288, 1170, 1141, and 1090. MS (ESI) m/e 274, 304, and 306. Anal. Calcd for $C_{19}H_{15}NO_3$: C, 74.74; H, 4.95; N, 4.59. Found C, 74.02; H, 5.02; N, 4.17.

4. Preparation of 5-Benzyl-11-methoxy-5H-benzo[b]carbazole-1-carboxylic acid, methyl ester

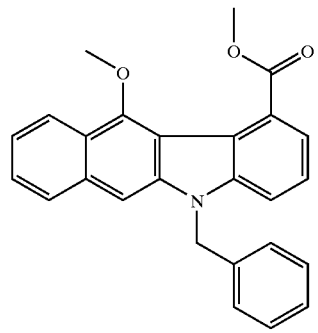

A solution of 11-methoxy-5H-benzo[b]carbazole-1-carboxylic acid, methyl ester, (0.458 g, 1.5 mM) in 5 mL DMF was added to a 60% NaH mineral oil dispersion (0.12 g, 3.0 mM, washed twice with hexane) at room temperature. Following cessation of gas evolution, benzyl bromide (0.20 mL, 0.288 g, 1.65 mM) was added and the mixture stirred at room temperature for 4 hours. The mixture was diluted with ethyl acetate and $H_2O$, the solvent layers separated, and the aqueous layer extracted with ethyl acetate (4×25 mL). The combined ethyl acetate extracts were washed with $H_2O$, 1N HCl, saturated aqueous $NaHCO_3$ solution, and saturated brine, dried over magnesium sulfate, filtered, concentrated in vacuo, and triturated with hexanes. The resultant yellow-orange gum was purified by column chromatography on silica gel (elution with 9:1 toluene/ethyl acetate) to afford 0.51 g (86%) of the title compound 5-benzyl-11-methoxy-5H-benzo[b]carbazole-1-carboxylic acid, methyl ester as a yellow-orange foam (MW 395.46).

$^1$H NMR (CDCl$_3$) δ 8.28 (d, 1H, J=9 Hz), 7.88 (d, 1H, J=9 Hz), 7.51–7.17 (m, 11H), 5.55 (s, 2H), 4.04 (s, 3H), and 3.94 (s, 3H). IR (CHCl$_3$, cm$^{-1}$) 3100–2850 (multiple peak grouping), 1725, 1634, 1596, 1453, 1346, 1310, 1287, 1171, and 1114. MS (ESI) m/e 364, 396. MS (FD) m/e 395. Anal. Calcd for $C_{26}H_{21}NO_3$: C, 78.97; H, 5.35; N, 3.54. Found C, 78.38; H, 5.27; N, 3.53.

5. Preparation of 5-Benzyl-11-hydroxy-5H-benzo[b]carbazole-1-carboxylic acid, methyl ester

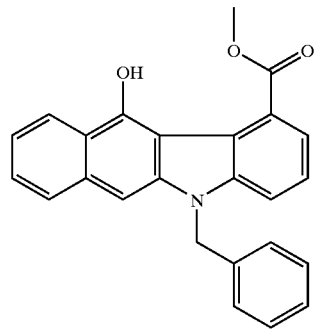

Boron tribromide (0.148 mL, 1.56 mM) was slowly added to a stirred solution of 5-benzyl-11-methoxy-5H-benzo[b]carbazole-1-carboxylic acid, methyl ester, (0.474 g, 1.2 mM)

in 8 mL methylene chloride at −10° C. After 1.5 h, the mixture was quenched with methanol (1.22 mL, 30.0 mM) and allowed to warm to room temperature with stirring over 2 h. The mixture was diluted with methylene chloride, washed with H₂O, 1N HCl, saturated aqueous NaHCO₃ solution, and saturated brine, dried over magnesium sulfate, filtered, and concentrated in vacuo. The resultant orange-brown solid was purified by column chromatography on silica gel (elution with gradient hexane/ethyl acetate) to afford 0.245 g (47%) of the title compound 5-benzyl-11-hydroxy-5H-benzo[b]carbazole-1-carboxylic acid, methyl ester as an orange foam (MW 381.44).

¹H NMR (CDCl₃) δ 11.14 (br s, 1H), 8.60 (d, 1H, J=8 Hz), 7.94 (br s, 1H), 7.75 (br s, 1H), 7.51–7.41 (m, 2H), 7.37–7.33 (t, 1H, J=7 Hz), 7.26–7.21 (m, 5H), 7.12 (d, 2H, J=6 Hz), 5.55 (s, 2H), and 4.15 (s, 3H). IR (KBr, cm⁻¹) 3420 (br), 3050–2940 (multiple peak grouping), 1727, 1652, 1628, 1452, 1438, 1279, 1197, 1179, and 747. MS (ESI) m/e 350, 364, 380, and 382. Anal. Calcd for $C_{25}H_{19}NO_3$: C, 78.72; H, 5.02; N, 3.67. Found C, 77.43; H, 4.78; N, 3.55.

6. Preparation of 5-Benzyl-11-hydroxy-5H-benzo[b]carbazole-1-carboxylic acid amide

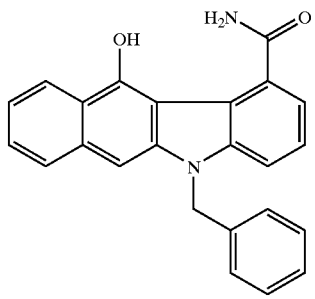

A solution of 5-benzyl-11-hydroxy-5H-benzo[b]carbazole-1-carboxylic acid, methyl ester, (0.229 g, 0.60 mM) in 8 mL THF was placed in an Ace Glass pressure tube (203 mm×38 mm) with a small stirring bar. A N₂(g) stream was installed over the solution surface. The pressure tube and reaction solution were cooled to −78° C., and ~8 mL NH₃(l) was condensed into the reaction vessel by introduction of an NH₃(g) stream. The pressure tube was sealed with a teflon O-ring screw cap, the resultant orange solution stirred at −78° C. for 10 minutes, then the cooling bath was removed and the reaction solution allowed to warm to ambient temperature behind a blast shield. After 48 h, the pressure tube was re-cooled to −78° C. and the internal NH₃(g) pressure was released by careful removal of the Teflon™ cap. The reaction solution was allowed to slowly warm to room temperature while NH₃(g) bubbled off, then the solution was concentrated in vacuo to afford 0.22 g (99%) of the title compound 5-benzyl-11-hydroxy-5H-benzo[b]carbazole-1-carboxylic acid amide as a yellowish-green solid (MW 366.42).

¹H NMR (DMSO-d6) δ 11.52 (s, 1H), 9.08 (br s, 1H), 8.63 (br s, 1H), 8.37 (d, 1H, J=8 Hz), 7.80 (d, 2H, J=8 Hz), 7.73 (d, 1H, J=6 Hz), 7.53–7.42 (m, 5H), 7.29–7.11 (m, 4H), and 5.69 (s, 2H). IR (KBr, cm⁻¹) 3480–2920 (multiple peak grouping), 1725, 1658, 1645, 1631, 1594, 1578, 1440, 1295, and 749. MS (ESI) m/e 350, 365, and 367. Anal. Calcd for $C_{24}H_{18}N_2O_2$: C, 78.67; H, 4.95; N, 7.65. Found C, 76.10; H, 5.17; N, 6.20.

7. Preparation of (5-Benzyl-1-carbamoyl-5H-benzo[b]carbazol-11-yloxy)-acetic acid, methyl ester

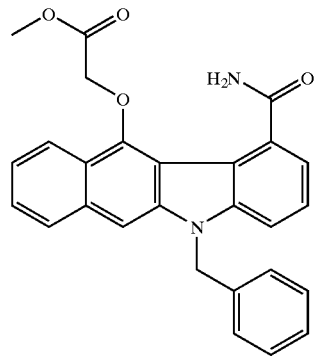

40% Methanolic Triton B (0.378 mL, 0.832 mM) was added to a solution of 5-benzyl-11-hydroxy-5H-benzo[b]carbazole-1-carboxylic acid amide, (0.235 g, 0.64 mM) in 5 mL DMF at room temperature. After 2 minutes, methyl bromoacetate (0.125 mL, 0.202 g, 1.28 mM) was added and the resultant mixture stirred at room temperature for 2 h. Cesium carbonate (0.105 g, 0.32 mM) was then added as a solid, and the mixture allowed to stir at room temperature for an additional 1 h. The mixture was diluted with ethyl acetate, washed with H₂O, 1N HCl, saturated aqueous NaHCO₃ solution, and saturated brine, dried over magnesium sulfate, filtered, and concentrated in vacuo. The resulting brown residue-was purified by column chromatography on silica gel (elution with ethyl acetate) to afford 0.151 g (53%) of the title compound (5-benzyl- 1-carbamoyl-5H-benzo[b]carbazol-11-yloxy)-acetic acid, methyl ester as a brown foam (MP 120–125° C., MW 438.49).

¹H NMR (CDCl₃) δ 8.30 (d, 1H, J=9 Hz), 8.05 (d, 1H, J=9 Hz), 7.51–7.46 (m, 3H), 7.36–7.26 (m, 7H), 7.18 (d, 1H, J=8 Hz), 5.91 (br s, 2H), 5.81 (s, 2H), 4.72 (s, 2H), and 3.72 (s, 3H). IR (KBr, cm⁻¹) 3430, 3330, 3150–2830 (multiple peak grouping), 1735, 1659, 1595, 1436, 1393, 1213, 1158, and 750. MS (ESI) m/e 422, 439. MS (FD) m/e 438. Anal. Calcd for $C_{27}H_{22}N_2O_4$: C, 73.96; H, 5.06; N, 6.39. Found C, 70.52; H, 5.39; N, 5.42.

Preparation of (5-Benzyl-1-carbamoyl-5H-benzo[b]carbazol-11-yloxy)-acetic acid, sodium salt

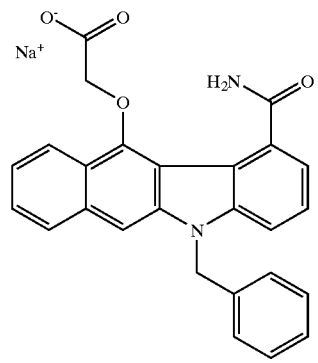

A solution of (5-benzyl-1-carbamoyl-5H-benzo[b]carbazol-11-yloxy)-acetic acid, methyl ester, (0.088 g, 0.2 mM) and 1N NaOH (0.22 mL, 0.22 mM) in 5 mL of ethanol was stirred for 3.5 h at 25° C. A small volume of diethyl ether/hexanes was added, then the mixture was cooled in the refrigerator. The resultant yellowish-brown precipitate was collected by filtration, washed with a small amount of EtOH/diethyl ether/hexanes, then dried in vacuo to afford 0.065 g (73%) of the title compound (5-benzyl-1-carbamoyl-5H-benzo[b]carbazol-11-yloxy)-acetic acid, sodium salt as a brown solid (MW 446.44, exact mass minus sodium 423.13).

$^1$H NMR (DMSO-d6) δ 8.44 (d, 1H, J=8 Hz), 8.23 (br s, 1H), 7.97 (d, 1H, J=8 Hz), 7.51–7.38 (m, 4H), 7.36–7.06 (m, 8H), 5.78(s, 2H), and 4.18 (s, 2H). IR (kBr, cm$^{-1}$) 3426, 3061, 1728, 1664, 1594, 1495, 1419, 1380, 1347, 1321, 1305, 1264, 1216, 1157, 1013, 750, and 696. MS (ESI) m/e 425. MS (FAB) m/e 447. Anal. Calcd for $C_{26}H_{19}N_2NaO_4$: C, 69.95; H, 4.29; N, 6.27. Found C, 65.21; H, 4.42; N, 5.06.

EXAMPLE 2

(5-Benzyl-1-carbamoyl-7,8,9,10-tetrahydro-5H-benzo[b]carbazol-11-yloxy)-acetic acid, sodium salt

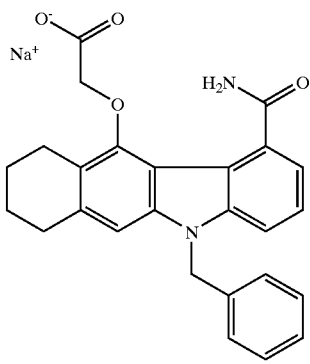

1. Preparation of 2-Bromo-5,6,7,8-tetrahydronaphthalen-1-ol

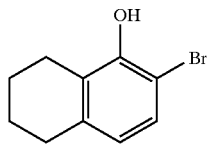

To a stirred mixture of 5,6,7,8-tetrahydronaphthalen-1-ol (29.2 g, 195 mmol) in dichloromethane (300 mL) was added diisopropylamine (2.75 mL, 19.5 mmol) at room temperature. The reaction mixture was cooled to 0° C., and N-bromosuccinimide (36.62 g, 205 mmol) dissolved in dichloromethane (1.0 L) was added dropwise over 6.5 h. The mixture was then allowed to stir at room temperature for an additional 1 h. At this point 1N HCl was slowly added until the mixture reached pH 1, added H$_2$O (100 mL), separated the dichloromethane solvent layer, dried the organic extracts over anhydrous sodium sulfate, and filtered. Concentrated the filtrate in vacuo at ambient temperature to produce a clear oil, added hexane (1.0 L) to precipitate unreacted N-bromosuccinimide, collected the resulting precipitate and washed with hexane. The filtrate was concentrated in vacuo, and the resultant oil purified by column chromatography on silica gel (elution with 2.5% ethyl acetate/hexane) to afford 32.3 g (73%) of the title compound of 2-bromo-5,6,7,8-tetrahydronaphthalen-1-ol as an off-white solid (MW 227.10, $C_{10}H_{11}BrO$).

$^1$H NMR (DMSO-d$_6$) δ 8.73 (s, 1H), 7.13 (d, 1H, J=8 Hz), 6.46 (d, 1H, J=8 Hz), 2.56–2.55 (m, 4H), and 1.69–1.58 (m, 4H). MS (ESI) m/e 225, 227 (negative ions).

2. Preparation of 6-Bromo-5-methoxy-1,2,3,4-tetrahydronaphthalene

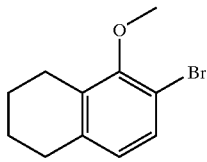

A solution of 2-bromo-5,6,7,8-tetrahydronaphthalen-1-ol, (28 g, 123.3 mmol), iodomethane (23.09 mL, 52.66 g, 371 mmol), and potassium carbonate (51.52 g, 373.3 mmol) in DMF (450 mL) was stirred at room temperature for 48 h. The mixture was poured into H$_2$O (500 mL) and extracted with ethyl acetate (4×250 mL). The organic extracts were combined, washed with H$_2$O (4×250 mL), dried over anhydrous sodium sulfate, filtered, and concentrated in vacuo to afford 29.6 g (quantitative yield) of the title compound 6-bromo-5-methoxy-1,2,3,4-tetrahydronaphthalene as a pale yellow oil (MW 241.13, $C_{11}H_{13}BrO$).

$^1$H NMR (DMSO-d$_6$) δ 7.24 (d, 1H, J=8 Hz), 6.73 (d, 1H, J=8 Hz), 3.65 (s, 3H), 2.67–2.59 (m, 4H), and 1.66–1.63 (m, 4H).

3. Preparation of 1-Methoxy-5,6,7,8-tetrahydronaphthalene-2-boronic acid

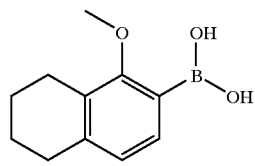

To a stirred mixture of 6-bromo-5-methoxy-1,2,3,4-tetrahydronaphthalene, (15 g, 62.21 mmol) in THF (150 mL) cooled to 0° C. was added n-butyllithium (43.14 mL, 69.03 mmol, 1.6M solution in hexanes) over 5 min. The reaction mixture was stirred for 1 h then cooled to −78° C., and triisopropyl borate (21.72 mL, 17.7 g, 94.14 mmol) was added dropwise over 0.25 h. The mixture was allowed to warm to room temperature with stirring then poured into 1N HCl (100 mL). The product was extracted with ethyl acetate (4×100 mL), the combined organic extracts dried over anhydrous sodium sulfate, and filtered. After concentrating the filtrate in vacuo at ambient temperature, the oily yellow residue was partially dissolved in diethyl ether, triturated with hexane, and the resulting precipitate filtered and washed with hexane to afford 1.64 g (13%) of the title compound 1-methoxy-5,6,7,8-tetrahydronaphthalene-2-boronic acid as an off-white crystalline solid (MW 206.05, $C_{11}H_{15}BO_3$).

¹H NMR (DMSO-d₆) δ 7.79 (s, 2H), 7.18 (d, 1H, J=8 Hz), 6.75 (d, 1H, J=8 Hz), 3.64 (s, 3H), 2.67–2.64 (m, 2H), 2.61–2.59 (m, 2H) and 1.67–1.65 (m, 4H).

4. Preparation of 2-Chloro-3-nitrobenzoic acid, methyl ester

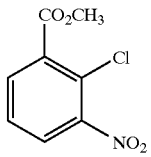

A solution of 2-chloro-3-nitrobenzoic acid (20.16 g, 100 mmol), iodomethane (15.6 g, 110 mmol), and potassium carbonate (15.0 g, 108.5 mmol) in DMF (100 mL) was stirred at room temperature for 48 hours. The mixture was poured into 1.5 liters of H₂O. The resultant precipitate was collected by filtration, washed with H₂O, and dried in vacuo to afford 20.0 g (93%) of the title compound 2-chloro-3-nitrobenzoic acid, methyl ester as a white solid (MW 215.59).

¹H NMR (CDCl₃) δ 8.42 (dd, 1H, J=1 and 8 Hz), 8.18 (dd, 1H, J=1 and 8 Hz), 7.43 (t, 1H, J=8 Hz), and 3.9 (s, 3H).

IR (KBr, cm⁻¹) 1743, 1719, 1595, 1540, 1532, 1433, 1357, 1300, and 730. MS (FD) m/e 215, 216. Anal. Calcd for C₈H₆NClO₄: C, 44.57; H, 3.81; N, 6.50. Found C, 44.19; H, 3.45; N, 6.19.

5. Preparation of 2-(1-Methoxy-5,6,7,8-tetrahydronaphthalen-2-yl)-3-nitrobenzoic acid, methyl ester

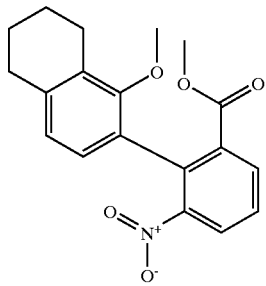

A solution of 2-chloro-3-nitrobenzoic acid, methyl ester, (2.06 g, 9.61 mM), 1-methoxy-5,6,7,8-tetrahydronaphthalene-2-boronic acid, (2.08 g, 10.09 mM), tetrakis(triphenylphosphine)palladium(0) (0.583 g, 0.5 mM), and 2M aqueous sodium carbonate solution (10.5 mL, 21.0 mM) in THF (50 mL) was stirred at reflux for 48 hours in the absence of light. The mixture was cooled to room temperature, the THF removed in vacuo, and the resulting aqueous residue dissolved in ethyl acetate and brine. The solvent layers were separated, the aqueous layer extracted with ethyl acetate (4×25 mL), the combined ethyl acetate extracts washed successively with H₂O, 1N HCl, saturated aqueous NaHCO₃ solution, and saturated brine, dried over magnesium sulfate, filtered, and concentrated in vacuo. The resultant black oil was purified by column chromatography on silica gel (elution with 5–15% ethyl acetate/hexane) to afford 0.656 g (20%) of the title compound 2-(1-methoxy-5,6,7,8-tetrahydronaphthalen-2-yl)-3-nitrobenzoic acid, methyl ester as a yellow solid (MW 341.37, C₁₉H₁₉NO₅).

¹H NMR (DMSO-d₆) δ 8.10 (dd, 1H, J=1 and 8 Hz), 8.00 (dd, 1H, J=1 and 8 Hz), 7.70 (t, 1H, J=8 Hz), 6.84 (d, 1H, J=8 Hz), 6.78 (d, 1H, J=8 Hz), 3.54 (s, 3H), 3.22 (s, 3H), 2.71 (br s, 2H), 2.62–2.61 (m, 2H), and 1.70 (br s, 4H).

IR (CHCl₃, cm⁻¹) 2936, 1733, 1602, 1535, 1489, 1363, 1297, 1188, and 967. MS (ESI) m/e 342. MS (FD) m/e 341. Anal. Calcd for C₁₉H₁₉NO₅: C, 66.85; H, 5.61; N, 4.10. Found C, 66.00; H, 5.07; N, 3.37.

6. Preparation of 11-Methoxy-7,8,9,10-tetrahydro-5H-benzo[b]carbazole-1-carboxylic acid, methyl ester

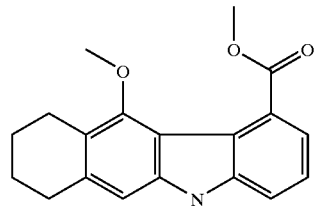

A solution of 2-(1-methoxy-5,6,7,8-tetrahydronaphthalen-2-yl)-3-nitrobenzoic acid, methyl ester, (0.5 g, 1.46 mM) in triphenyl phosphite (2.26 g, 1.91 mL, 7.29 mM) was heated at 160° C. for 48 h under a nitrogen atmosphere. The mixture was cooled to room temperature and dried azeotropically in vacuo with toluene, then purified by column chromatography on silica gel (elution with 10% ethyl acetate/hexane) to afford 0.2 g (44%) of the title compound 11-methoxy-7,8,9,10-tetrahydro-5H-benzo[b]carbazole-1-carboxylic acid, methyl ester as a tan solid (MP 194–196° C., MW 309.37).

¹H NMR (CDCl₃) δ 8.00 (br s, 1H), 7.42 (d, 1H, J=8 Hz), 7.36 (t, 1H, J=8 Hz), 7.27 (d, 1H, J=8 Hz), 6.93 (s, 1H), 3.95 (s, 3H), 3.67 (s, 3H), 2.93 (br s, 2H), 2.89 (br s, 2H), and 1.84–1.81 (m, 4H). IR (KBr, cm⁻¹) 3263, 2932, 2831, 1701, 1631, 1436, 1306, 1294, 1142, 983, 761, and 740. MS (ESI) m/e 278, 308, and 310. Anal. Calcd for C₁₉H₁₉NO₃: C, 73.77; H, 6.19; N, 4.53. Found C, 73.87; H, 6.15; N, 4.45.

7. Preparation of 5-Benzyl-11-methoxy-7,8,9,10-tetrahydro-5H-benzo[b]carbazole-1-carboxylic acid, methyl ester

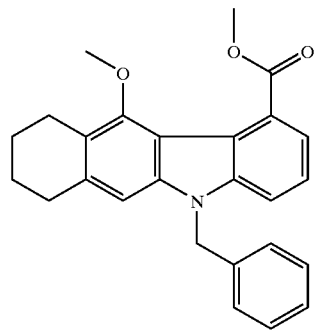

A solution of 11-methoxy-7,8,9,10-tetrahydro-5H-benzo[b]carbazole-1-carboxylic acid, methyl ester, (0.155 g, 0.5 mM) in 5 mL DMF was added to a 60% NaH mineral oil dispersion (0.04 g, 1.0 mM, washed twice with hexane) at room temperature. Following cessation of gas evolution, benzyl bromide (0.067 mL, 0.094 g, 0.55 mM) was added and the mixture stirred at room temperature for 3 h. The mixture was diluted with ethyl acetate and H₂O, the solvent layers separated, and the aqueous layer extracted with ethyl acetate (4×25 mL). The combined ethyl acetate extracts were washed with H₂O, 1N HCl, saturated aqueous NaHCO₃ solution, and saturated brine, dried over magnesium sulfate, filtered, concentrated in vacuo, and triturated with hexanes. The resultant tan solid was dried in vacuo, and purified by column chromatography on silica gel (elution with 9:1 toluene/ethyl acetate) to afford 0.133 g (66%) of the title compound 5-benzyl-11-methoxy-7,8,9,10-tetrahydro-5H-benzo[b]carbazole-1-carboxylic acid, methyl ester as an off-white foam (MP 144–146° C., MW 399.49).

$^1$H NMR (CDCl₃) δ 7.37–7.32 (m, 3H), 7.28–7.23 (m, 3H), 7.10 (d, 2H, J=8 Hz), 6.89 (s, 1H), 5.44 (s, 2H), 3.97 (s, 3H), 3.69 (s, 3H), 2.91–2.89 (m, 4H), and 1.83–1.81 (m, 4H). IR (KBr, cm$^{-1}$) 2934, 1734, 1453, 1427, 1304, 1277, 1169, 1135, 1109, 754, and 713. MS (ESI) m/e 368, 400. Anal. Calcd for C₂₆H₂₅NO₃: C, 78.17; H, 6.31; N, 3.51. Found C, 77.68; H, 6.31; N, 3.79

8. Preparation of 5-Benzyl-11-hydroxy-7,8,9,10-tetrahydro-5H-benzo[b]carbazole-1-carboxylic acid, methyl ester

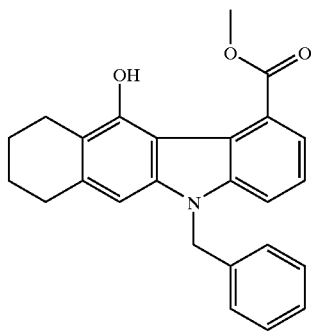

Boron tribromide (0.3 mL, 3.0 mM) was slowly added to a stirred solution of 5-benzyl-11-methoxy-7,8,9,10-tetrahydro-5H-benzo[b]carbazole-1-carboxylic acid, methyl ester, (0.12 g, 0.3 mM) in 5 mL methylene chloride at −10° C. After 5.5 h, the mixture was quenched with methanol (3.0 mL, 75.0 mM) and allowed to warm to room temperature with stirring over 2 h. The mixture was diluted with methylene chloride, washed with H₂O, 1N HCl, saturated aqueous NaHCO₃ solution, and saturated brine, dried over magnesium sulfate, filtered, and concentrated in vacuo to afford 0.108 g (93%) of the title compound 5-benzyl-11-hydroxy-7,8,9,10-tetrahydro-5H-benzo[b]carbazole-1-carboxylic acid, methyl ester as a yellow solid (MP 174–176° C., MW 385.47).

$^1$H NMR (CDCl₃) δ 10.41 (s, 1H), 7.92 (d, 1H, J=8 Hz), 7.49 (d, 1H, J=8 Hz), 7.34 (t, 1H, J=8 Hz), 7.27–7.21 (m, 3H), 7.07–7.05 (m, 2H), 6.67 (s, 1H), 5.47 (s, 2H), 4.09 (s, 3H), 2.90–2.87 (m, 4H), 1.87–1.80 (m, 2H), and 1.79–1.77 (m, 2H). IR (KBr, cm$^{-1}$) 3460 (br), 3130–2830 (multiple peak grouping), 1671, 1437, 1294, 1270, and 751. MS (ESI) m/e 354, 384, and 386. Anal. Calcd for C₂₅H₂₃NO₃: C, 77.90; H, 6.01; N, 3.63. Found C, 77.71; H, 6.10; N, 3.53.

9. Preparation of 5-Benzyl-11-hydroxy-7,8,9,10-tetrahydro-5H-benzo[b]carbazole-1-carboxylic acid amide

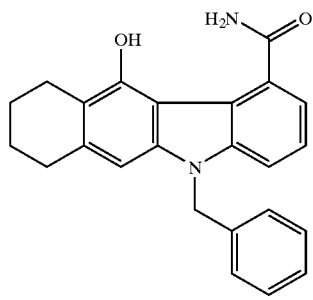

A solution of 5-benzyl-11-hydroxy-7,8,9,10-tetrahydro-5H-benzo[b]carbazol-1-carboxylic acid, methyl ester, (0.097 g, 0.25 mM) in 8 mL THF was placed in an Ace Glass pressure tube (203 mm×38 mm) with a small stirring bar. A N₂(g) stream was installed over the solution surface. The pressure tube and reaction solution were cooled to −78° C., and ~8 mL NH₃(l) was condensed into the reaction vessel by introduction of an NH₃(g) stream. The pressure tube was sealed with a teflon O-ring screw cap, the resultant brown solution stirred at −78° C. for 10 minutes, then the cooling bath was removed and the reaction solution allowed to warm to ambient temperature behind a blast shield. After 24 h, the pressure tube was re-cooled to −78° C. and the internal NH₃(g) pressure was released by careful removal of the Teflon cap. The reaction solution was allowed to slowly warm to room temperature while NH₃(g) bubbled off, then the solution was concentrated in vacuo to afford 0.92 g (quantitative) of the title compound 5-benzyl-11-hydroxy-7,8,9,10-tetrahydro-5H-benzo[b]carbazole-1-carboxylic acid amide as a tan solid (MP 225° C. dec, MW 370.46).

$^1$H NMR (DMSO-d6) δ 10.56 (s, 1H), 8.88 (br s, 1H), 8.40 (br s, 1H), 7.67 (dd, 1H, J=2 and 7 Hz), 7.40–7.34 (m, 2H), 7.22 (d, 1H, J=7 Hz), 7.19 (d, 2H, J=8 Hz), 7.09 (d, 2H, J=7 Hz), 6.79 (s, 1H), 5.58 (s, 2H), 2.81–2.78 (m, 2H), 2.69–2.66 (m, 2H), and 1.74–1.69 (m, 4H). IR (KBr, cm$^{-1}$) 3408, 3255, 2918, 2866, 2837, 1626, 1599, 1576, 1551, 1452, 1435, 1332, 1292, 1271, and 696. MS (ESI) m/e 354, 369, and 371. Anal. Calcd for C₂₄H₂₂N₂O₂: C, 77.81; H, 5.99; N, 7.56. Found C, 74.69; H, 6.08; N, 6.74.

10. Preparation of (5-Benzyl-1-carbamoyl-7,8,9,10-tetrahydro-5H-benzo[b]carbazol-11-yloxy)-acetic acid, methyl ester

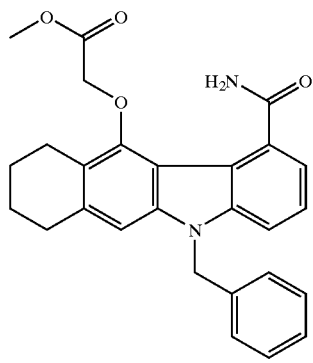

40% Methanolic Triton B (0.148 mL, 0.325 mM) was added to a solution of 5-benzyl-11-hydroxy-7,8,9,10-tetrahydro-5H-benzo[b]carbazole-1-carboxylic acid amide, (0.094 g, 0.25 mM) in 5 mL DMF at room temperature. After 2 minutes, methyl bromoacetate (0.049 mL, 0.076 g, 0.5 mM) was added and the resultant mixture stirred at room temperature for 2 h. Cesium carbonate (0.041 g, 0.125 mM) was then added as a solid, and the mixture allowed to stir at room temperature for an additional 2 h. The mixture was diluted with ethyl acetate, washed with $H_2O$, 1N HCl, saturated aqueous $NaHCO_3$ solution, and saturated brine, dried over magnesium sulfate, filtered, and concentrated in vacuo. The resulting tan foam was purified by column chromatography on silica gel (elution with ethyl acetate) to afford 0.035 g (31%) of the title compound (5-benzyl-1-carbamoyl-7,8,9,10-tetrahydro-5H-benzo[b]carbazol-11-yloxy)-acetic acid, methyl ester as a white solid (MP 174–177° C., MW 442.52).

$^1$H NMR (CDCl$_3$) δ 7.40–7.31 (m, 3H), 7.28–7.22 (m, 3H), 7.09 (d, 2H, J=6 Hz), 6.93 (s, 1H), 5.92 (br s, 1H), 5.76 (br s, 1H), 5.45 (s, 2H), 4.56 (s, 2H), 3.86 (s, 3H), 2.92–2.88 (m, 4H), and 1.82–1.80 (m, 4H). IR (KBr, cm$^{-1}$) 3457, 3110, 2929, 2854, 1767, 1677, 1592, 1440, 1205, 1183, 1175, and 699. MS (ESI) m/e 426, 443, and 465.

Anal. Calcd for $C_{27}H_{26}N_2O_4$: C, 73.29; H, 5.92; N, 6.33. Found C, 71.27; H, 5.70; N, 5.73.

11. Preparation of (5-Benzyl-1-carbamoyl-7,8,9,10-tetrahydro-5H-benzo[b]carbazol-11-yloxy)-acetic acid, sodium salt

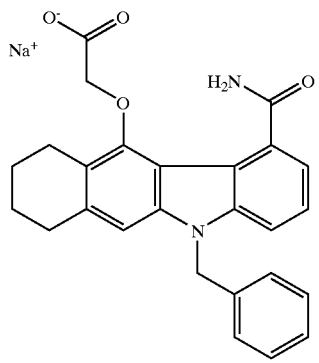

A solution of (5-benzyl-1-carbamoyl-7,8,9,10-tetrahydro-5H-benzo[b]carbazol-11-yloxy)-acetic acid, methyl ester, (0.027 g, 0.06 mM) and 1N NaOH (0.066 mL, 0.066 mM) in 5 mL of ethanol was stirred for 3 h at 25° C. A small volume of diethyl ether/hexanes was added, then the mixture was cooled in the refrigerator. The resultant white precipitate was collected by filtration, washed with a small amount of EtOH/diethyl ether/hexanes, then dried in vacuo to afford 0.019 g (70%) of the title compound (5-benzyl-1-carbamoyl-7,8,9,10-tetrahydro-5H-benzo[b]carbazol-11-yloxy)-acetic acid, sodium salt as a white solid (MW 450.47, exact mass minus sodium 427.17).

$^1$H NMR (DMSO-d6) δ 8.13 (br s, 1H), 7.51 (d, 1H, J=9 Hz), 7.32 (t, 1H, J=8 Hz) 7.25–7.17 (m, 4H), 7.07–7.02 (m, 4H), 5.57(s, 2H), 3.99 (s, 2H), 2.89–2.82 (m, 2H), 2.80-2.77 (m, 2H), and 1.77–1.66 (m, 4H). IR (KBr, cm$^{-1}$) 3380, 3170, 2935, 1702, 1675, 1622, 1596, 1448, 1455, 1437, 1420, 1302, and 1252. MS (ESI) m/e 412, 427, and 429. Anal. Calcd for $C_{26}H_{23}N_2NaO_4$: C, 69.32; H, 5.15; N, 6.22. Found C, 66.76; H, 4.95; N, 5.97.

EXAMPLE 3

1. 9-Benzyl-9H-1-thia-9,10-diaza-cyclopenta[b]fluorene-4-carboxylic acid amide

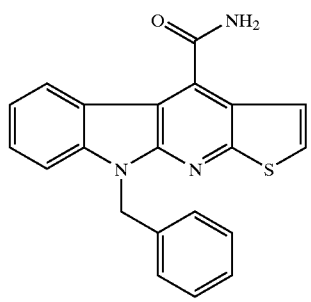

2. Preparation of 9-Benzyl-9H-1-thia-9,10-diaza-cyclopenta[b]fluorene-4-carboxylic acid

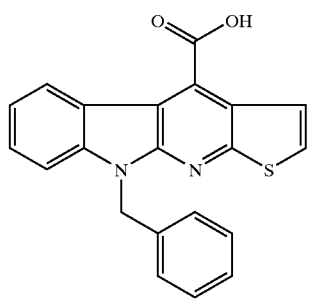

A solution of 9H-1-thia-9,10-diaza-cyclopenta[b]fluorene-4-carboxylic acid, methyl ester, (0.025 g, 0.089 mM) in 3 mL DMF was added to a 60% NaH mineral oil dispersion (0.007 g, 0.178 mM) at room temperature. Following cessation of gas evolution, benzyl bromide (0.012 mL, 0.017 g, 0.098 mM) was added and the mixture stirred at room temperature for 3.5 h. The mixture was diluted with ethyl acetate and $H_2O$, the solvent layers separated, and the aqueous layer extracted with ethyl acetate (4×25 mL). The combined ethyl acetate extracts were washed with $H_2O$, 1N HCl, saturated aqueous $NaHCO_3$ solution, and saturated brine, dried over magnesium sulfate, filtered, and concentrated in vacuo to afford 0.013 g of an oily solid that was identified as unreacted 9H-1-thia-9,10-diaza-cyclopenta[b]fluorene-4-carboxylic acid, methyl ester. Adjusted the above aqueous layer from the initial reaction workup to pH 1 with 1N HCl, and extracted with ethyl acetate (4×25 mL). The combined ethyl acetate extracts were washed with $H_2O$, 1N HCl, and saturated brine, dried over magnesium sulfate, filtered, and concentrated in vacuo to afford 0.023 g (74%) of the title compound 9-benzyl-9H-1-thia-9,10-diaza-cyclopenta[b]fluorene-4-carboxylic acid as a yellow solid (MW 358.42, $C_{21}H_{14}N_2O_2S$).

$^1$H NMR (CDCl$_3$) δ 8.67 (d, 1H, J=8 Hz), 7.90 (d, 1H, J=6 Hz), 7.50–7.47 (m, 2H), 7.39 (d, 1H, J=8 Hz), 7.30 (t, 1H, J=8 Hz), 7.26–7.23 (m, 5H), and 5.80 (s, 2H). MS (ESI) m/e 357, 359.

1. Preparation of 9-Benzyl-9H-1-thia-9,10-diaza-cyclopenta[b]fluorene-4-carboxylic acid amide

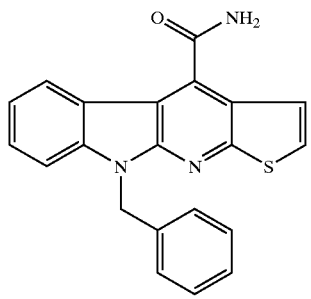

To a solution of 9-benzyl-9H-1-thia-9,10-diaza-cyclopenta[b]fluorene-4-carboxylic acid, (0.021 g, 0.06 mM) in 5 mL 1,2-dichloroethane was added oxalyl chloride (0.021 mL, 0.24 mM) and one drop of DMF. The mixture was stirred at room temperature for 1 h, then concentrated and dried azeotropically in vacuo with toluene. Dissolved the resultant yellow solid in 5 mL 1,2-dichloroethane and placed in an Ace Glass pressure tube (203 mm×38 mm) with a small stirring bar. A $N_2$(g) stream was installed over the solution surface. The pressure tube and reaction solution were cooled to −78° C., and ~5 mL $NH_3$ (1) was condensed into the reaction vessel by introduction of an $NH_3$(g) stream. The pressure tube was sealed with a teflon O-ring screw cap, the resultant yellow solution stirred at −78° C. for 10 minutes, then the cooling bath was removed and the reaction solution allowed to warm to ambient temperature behind a blast shield. After 72 h, the pressure tube was re-cooled to −78° C. and the internal $NH_3$ (g) pressure was released by careful removal of the Teflon cap. The reaction solution was allowed to slowly warm to room temperature while $NH_3$(g) bubbled off, then the solution was concentrated in vacuo to afford 0.015 g (71%) of the title compound 9-benzyl-9H-1-thia-9,10-diaza-cyclopenta[b]fluorene-4-carboxylic acid amide as a yellow solid (MP 242–245° C., MW 357.44).

$^1$H NMR (CDCl$_3$) δ 8.37 (d, 1H, J=8 Hz), 7.57 (d, 1H, J=6 Hz), 7.47 (t, 1H, J=7 Hz), 7.41 (d, 1H, J=6 Hz), 7.35 (d, 1H, J=8 Hz), 7.29 (t, 1H, J=6 Hz), 7.27–7.20 (m, 4H), 6.96 (s, 1H), 6.22 (br s, 1H), 6.19 (br s, 1H), and 5.74 (s, 2H). IR (KBr, cm$^{-1}$) 3365, 3181, 3090, 2953, 2923, 2852, 1645, 1575, 1470, 1419, 1295, 1128, and 743. MS (ESI) m/e 356, 358. Anal. Calcd for $C_{21}H_{15}N_3OS$: C, 70.57; H, 4.23; N, 11.76. Found C, 69.75; H, 5.72; N, 8.56.

We claim:

1. A tetracyclic compound of formula (I), or a pharmaceutically acceptable salt, solvate or prodrug thereof:

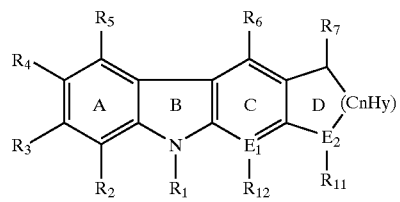

(I)

wherein;

$E_1$ is C or N with the appropriate number of hydrogen atoms or non-interfering groups appended; $E_2$ is C, N or S with the appropriate number of hydrogen atoms or non-interfering groups appended where applicable or $E_2$ is oxygen wherein $R_{11}$ is non-existent;

n is 1, 2 or 3 and y is an appropriate number of hydrogen atoms based on the value of (n) and also based on ring unsaturation;

$R_1$ is selected from group (a), (b), or (c) wherein;

(a) is $C_7$–$C_{20}$ alkyl, $C_7$–$C_{20}$ haloalkyl, $C_7$–$C_{20}$ alkenyl, $C_7$–$C_{20}$ alkynyl or heterocyclic radical, or (b) is a member of (a) substituted with one or more independently selected from hydrogen, ($C_1$–$C_8$) alkyl, ($C_2$–$C_8$)alkenyl, ($C_2$–$C_8$)alkynyl, ($C_7$–$C_{12}$) aralkyl, ($C_7$–$C_{12}$)alkaryl, ($C_3$–$C_8$)cycloalkyl, ($C_3$–$C_8$)cycloalkenyl, phenyl, toluyl, xylenyl, biphenyl, ($C_1$–$C_8$)alkoxy, ($C_2$–$C_8$)alkenyloxy, ($C_2$–$C_8$) alkynyloxy, ($C_2$–$C_{12}$)alkoxyalkyl, ($C_2$–$C_{12}$)alkoxyalkyloxy, ($C_2$–$C_{12}$)alkylcarbonyl;

(c) is the group —(L)—$R_{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$, $R_3$, and $R_4$ are independently hydrogen, or a group containing 1 to 10 non-hydrogen atoms plus any required hydrogen atoms;

$R_5$ is —($L_5$)—Z, where —($L_5$)— is a divalent linker group selected from a bond, or a divalent group selected from:

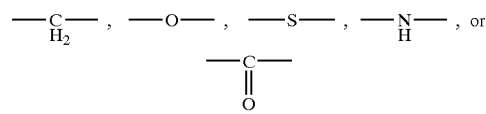

and Z is selected from an amide, thioamide, oxime amide, oxime thioamide, glyoxylamide, hydrazide, ureido or acetamide group represented by the formulae,

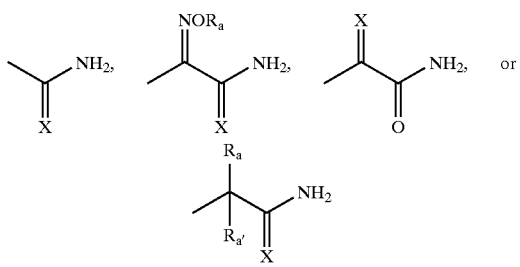

wherein X is oxygen or sulfur, $R_a$ and $R_{a'}$ are independently selected from hydrogen, ($C_1$–$C_8$)alkyl, aryl, ($C_1$–$C_8$)alkaryl, ($C_1$–$C_8$)alkoxy, aralkyl and —CN;

$R_6$ is the group, hydrogen, $CONH_2$, —CONHR$^{6b}$ or —($L_a$)—(acidic group) wherein —($L_a$)—, is an acid linker having an acid linker length of 1 to 8;

or the group —(L_h)—(N-hydroxyfunctional amide group); wherein —(L_h)—, is an N-hydroxyfunctional amide linker having a N-hydroxyfunctional amide linker length of 1 to 8; and wherein a N-hydroxyfunctional amide group is represented by the formula:

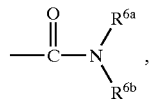

wherein Y is oxygen;
$R^{6a}$ is selected from the group consisting of OH, $(C_1-C_6)$ alkoxy, and aryloxy; and
wherein $R^{6b}$ is hydrogen or an organic substituent selected from the group consisting of $(C_1-C_8)$alkyl, aryl, $(C_7-C_{14})$ aralkyl, $(C_7-C_{14})$alkaryl, $(C_3-C_8)$cycloalkyl, $(C_1-C_8)$ alkoxyalkyl and these groups substituted with halogen, —$CF_3$, —OH, $(C_1-C_8)$alkyl, amino, carbonyl, and —CN;
  or $R_6$ is the group —(Lc)—(acylamino acid group) —wherein the "acylamino acid group" is represented by the formula:

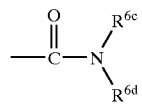

wherein $R^{6c}$ is selected from the group consisting of H, $(C_1-C_6)$alkyl, $(C_1-C_6)$alkoxy, heteroaryl and aryl, —$CF_3$; and wherein $NR^{6d}$ is an amino acid residue of an amino acid with the nitrogen atom being part of the amino group of the amino acid,
  $R_7$ is selected from hydrogen, $(C_1-C_8)$alkyl, $(C_2-C_8)$ alkenyl, $(C_2-C_8)$alkynyl, $(C_7-C_{12})$aralkyl, $(C_7-C_{12})$ alkaryl, $(C_3-C_8)$cycloalkyl, $(C_3-C_8)$cycloalkenyl, phenyl, toluyl, xylenyl, biphenyl, $(C_1-C_8)$alkoxy, $(C_2-C_8)$ alkenyloxy, $(C_2-C_8)$alkynyloxy, $(C_2-C_{12})$alkoxyalkyl, $(C_2-C_{12})$alkoxyalkyloxy, $(C_2-C_{12})$alkylcarbonyl, the group —(L_h)—(N-hydroxyfunctional amide group), or the group —(L_c)-acylamino acid group), or the group, —(L_a)—(acidic group); wherein —(L_a)—, is an acid linker having an acid linker length of 1 to 8;
  $R^{11}$ is hydrogen or non-existent, and $R^{12}$ is hydrogen or non-existent.

2. The compound of claim 1 wherein $E_1$ and $E_2$ are independently carbon and $R_2$, $R_3$, and $R_4$ are independently hydrogen, $(C_1-C_4)$alkyl, $(C_2-C_4)$alkenyl, —O—$(C_1-C_3$ alkyl), —S—$(C_1-C_3$ alkyl), $(C_3-C_4)$cycloalkyl, —$CF_3$, halo, —$NO_2$, —CN, or —$SO_3$.

3. The compound of claim 1 wherein the D ring has 1, 2 or 3 double bonds depending on ring size.

4. A compound according to claim 1 wherein $E_1$ and $E_2$ are both carbon.

5. The compound of claim 1 wherein the N-hydroxyfunctional amide linker group, —(L_h)—, or the acid linker —(L_a)—, or the acylamino acid linker —(L_c)—, for $R_6$ is selected from a group represented by the formula;

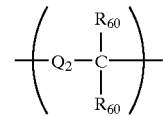

where $Q_2$ is selected from the group —$(CH_2)$—, —O—, —NH—, —C(O)—, and —S—, and each $R_{60}$ is independently selected from hydrogen, $(C_1-C_8)$alkyl, aryl, $(C_1-C_8)$ alkaryl, $(C_1-C_8)$alkoxy, aralkyl, and halo.

6. The compound of claim 1 wherein the N-hydroxyfunctional amide linker group, —(L_h)—, or the acid linker —(L_a)—, or the acylamino acid linker —(L_c)—, for $R_6$ is a divalent group independently selected from,

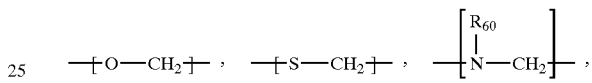

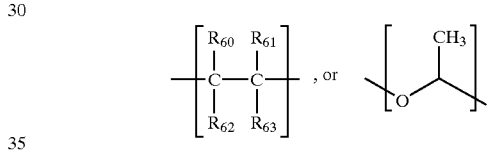

where $R_{60}$, $R_{61}$, $R_{62}$, and $R_{63}$ are independently selected from hydrogen, $(C_1-C_8)$alkyl.

7. The compound of claim 1 wherein for $R_5$, Z is the group represented by the formula;

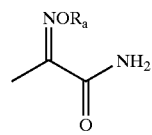

and the linking group —(L_5)— is a bond; and $R_a$ is hydrogen, methyl, ethyl, propyl, isopropyl, phenyl or benzyl.

8. The compound of claim 1 wherein for $R_5$, Z is the group represented by the formula;

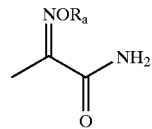

and the linking group —(L_5)— is a bond; and $R_a$ is hydrogen.

9. The compound of claim 1 wherein for $R_5$, Z is the group represented by the formula;

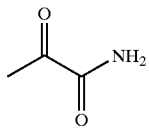

and the linking group —($L_5$)— is a bond.

10. The compound of claim 1 wherein for $R_5$, Z is the group represented by the formula;

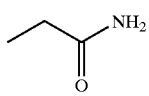

and the linking group —($L_5$)— is a bond.

11. The compound of claim 1 wherein for $R_5$ the divalent linking group —($L_5$)— is a bond.

12. The compound of claim 1 wherein $R_6$ is the group, —($L_c$)—(N-hydroxyfunctional amide group) and wherein the (N-hydroxyfunctional amide group) is:

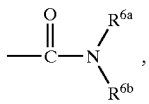

and $R^{6a}$ is independently selected from the group consisting of hydrogen, —OH, ($C_1$–$C_6$)alkoxy, and aryloxy; and wherein $R^{6b}$ is independently selected from the group consisting of H, ($C_1$–$C_6$)alkyl, arylalkyl, heteroaryl and aryl.

13. The compound of claim 1 wherein $R_6$ is the group, —($L_c$)—(acylamino acid group) and wherein the (acylamino acid group) is:

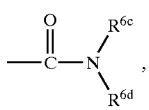

and $R^{6c}$ is selected from the group consisting of H, ($C_1$–$C_6$) alkyl, ($C_1$–$C_6$)alkoxy, heteroaryl and aryl; and wherein $NR^{6d}$ is an amino acid residue of a natural or unnatural amino acid with the nitrogen atom being part of the amino group of the amino acid.

14. The compound of claim 1 wherein $R_6$ is the group, —(La)—(acidic group) and wherein the (acidic group) is selected from the group consisting of —COOH, —COONa, and —COOK.

15. A tetracyclic compound represented by the formula (II′), or a pharmaceutically acceptable salt, solvate, or prodrug derivative thereof;

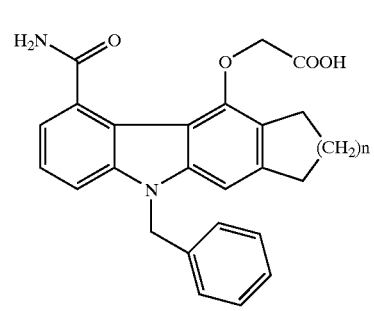

wherein;
n is 1 or 2.

16. A tetracyclic compound represented by the formula (III′), or a pharmaceutically acceptable salt, solvate, or prodrug derivative thereof;

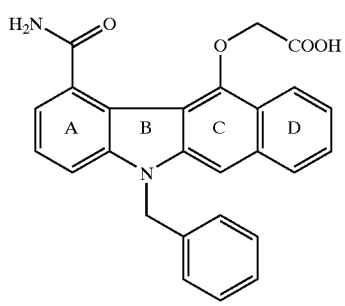

17. A compound according to compound selected from the group consisting of:
(10-Benzyl-6-carbamoyl-1,2,3,10-tetraydrocyclopenta[a] carbazol-5-yloxy)acetic acid methyl ester, (10-Benzyl-6-carbamoyl-1,2,3,10-tetraydrocyclopenta[a]carbazol-5-yloxy)acetic acid,
(10-Benzyl-6-carbamoyl-1,2,3,10-tetraydrocyclopenta[a] carbazol-5-yloxy)acetic acid methyl ester,
10-Benzyl-6-carbamoyl-1,2,3,10-tetraydrocyclopenta[a] carbazol-5-yloxy)acetic acid,
(11-Benzyl-7-carbamoyl-2,3,4,11-tetraydro-1H-benzo[a] carbazol-6-yloxy)acetic acid methyl ester, and
(11-Benzyl-7-carbamoyl-2,3,4,11-tetraydro-1H-benzo[a] carbazol-6-yloxy)acetic acid,
or a pharmaceutically acceptable salt, solvate or prodrug thereof.

18. A tetracyclic compound represented by the formulae (C1), (C2), (C3) (C4), or (C5):

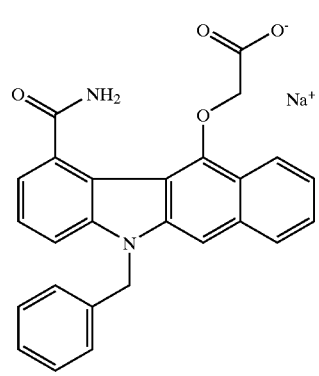

-continued
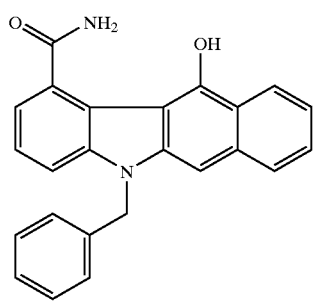
(C2)
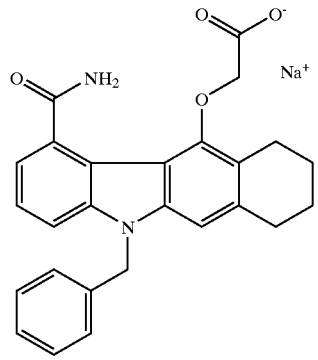
(C4)
(C3)
(C5)
19. A pharmaceutical formulation comprising a tetracyclic compound of claim 1 together with a pharmaceutically acceptable carrier or diluent.
* * * * *

UNITED STATES PATENT AND TRADEMARK OFFICE
CERTIFICATE OF CORRECTION

PATENT NO. : 6,992,100 B2  
APPLICATION NO. : 10/450745  
DATED : January 31, 2006  
INVENTOR(S) : Douglas Wade Beight It is certified that error appears in the above-identified patent and that said Letters Patent is hereby corrected as shown below:

In column 12, line 45, remove the rectangular box.

In column 17, line 60, in formula II, delete "$R^{8a}$" and replace with --$R^{6a}$--.

In column 28, line 15, delete ", and" and replace with --;--.

In column 80, line 33, delete "according to compound".

In column 80, line 36, start the next line (line 37) at (10-Benzl…), immediately after the comma.

Signed and Sealed this

Twelfth Day of December, 2006

JON W. DUDAS  
*Director of the United States Patent and Trademark Office*